(12) United States Patent
Richards et al.

(10) Patent No.: US 8,703,822 B2
(45) Date of Patent: Apr. 22, 2014

(54) METHOD FOR REMOVING UNDIFFERENTIATED AND DEDIFFERENTIATED STEM CELL

(75) Inventors: Mark Richards, Singapore (SG); Chee Wee Phoon, Singapore (SG); Mun Kin Lee, Singapore (SG)

(73) Assignee: Nanyang Polytechnic, Singapore (SG)

( * ) Notice: Subject to any disclaimer, the term of this patent is extended or adjusted under 35 U.S.C. 154(b) by 0 days.

(21) Appl. No.: 13/377,130

(22) PCT Filed: Jun. 11, 2010

(86) PCT No.: PCT/SG2010/000221
§ 371 (c)(1),
(2), (4) Date: Dec. 27, 2011

(87) PCT Pub. No.: WO2010/144059
PCT Pub. Date: Dec. 16, 2010

(65) Prior Publication Data
US 2012/0083532 A1    Apr. 5, 2012

Related U.S. Application Data

(60) Provisional application No. 61/186,762, filed on Jun. 12, 2009.

(51) Int. Cl.
| | |
|---|---|
| *A01N 47/28* | (2006.01) |
| *A61K 31/17* | (2006.01) |
| *A61K 31/165* | (2006.01) |
| *C12N 5/071* | (2010.01) |

(52) U.S. Cl.
USPC ........................... 514/595; 435/377; 514/625

(58) Field of Classification Search
USPC .................................. 514/595, 625; 435/377
See application file for complete search history.

(56) References Cited

U.S. PATENT DOCUMENTS

| | | |
|---|---|---|
| 2003/0069307 A1 | 4/2003 | Ley |
| 2009/0076019 A1 | 3/2009 | Tyers et al. |

FOREIGN PATENT DOCUMENTS

| | | |
|---|---|---|
| EP | 1 284 145 A1 | 2/2003 |
| WO | WO 01/59067 A2 | 8/2001 |
| WO | WO 2009/004071 A1 | 1/2009 |

OTHER PUBLICATIONS

Naujok et al. Stem Cell Rev and Rep (2010) 6:450-461.*

(Continued)

*Primary Examiner* — Savitha Rao
*Assistant Examiner* — Angela Brown-Pettigrew
(74) *Attorney, Agent, or Firm* — Christie, Parker & Hale, LLP

(57) ABSTRACT

The present invention relates to a method of removing undifferentiated stem cells and dedifferentiated stem cells from a sample of cells. The invention further relates to preventing dedifferentiation of differentiated cells. Both methods comprise of administering to said cells an effective amount of compounds of formula (I):

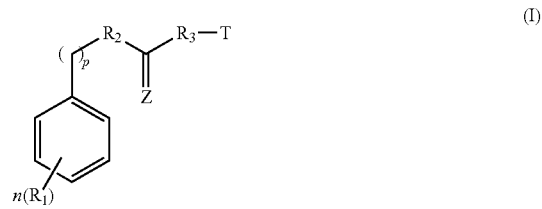

or a pharmaceutically acceptable salt thereof, wherein $R_1$, $R_2$, $R_3$, n, p, Z and T are defined herein.

11 Claims, 12 Drawing Sheets

(56) References Cited

OTHER PUBLICATIONS

Prasad S Koka. Stem Cells Research Compendium, vol. 1 (2008) p. 316.*

International Search Report and Written Opinion of corresponding International Application No. PCT/SG2010/000221, dated Dec. 10, 2010, 9 pages.

Diamandis, Phedias et al.; "Chemical genetics reveals a complex functional ground state of neural stem cells"; Nature Chemical Biology; Letters; vol. 3; No. 5; May 2007; pp. 268-273 (6pp.).

Extended European Search Report for corresponding European Application No. 10786472.0 dated Jul. 2, 2013; 9pp.

Lee, Seong-Ae et al.; "Capsaicin promotes the development of burst-forming units-erythroid (BFU-E) from mouse bone marrow cells"; Experimental and Molecular Medicine; vol. 39; No. 3; Jun. 2007; pp. 278-283 (6pp.).

Walpole, Christopher S. J. et al.; "Analogues of Capsaicin with Agonist Activity as Novel Analgesic Agents; Structure-Activity Studies. 1. The Aromatic "A-Region""; J. Med. Chem.; vol. 36; 1993; American Chemical Society; pp. 2362-2372 (11pp.).

* cited by examiner

Wicell, H1, 70P

JC010, 40 μM, 24 h    JC011, 40 μM, 24 h    JC010, 40 μM, 12 h

Effects of Capsaicin Analogues on hESCs & MEF feeder growth after 24 h incubation. (A) DMSO control, (B) JC010, 2.5 µg/mL (8 µM), (C) JC010, 12.5 µg/mL, (D) JC005, 12.5 µg/mL, (E) JC011, 2.5 µg/mL, (F) JC011, 12.5 µg/mL.

Untreated hESC    +JC011, 40 µM

+JC011, 24 h, 40 µM    +JC011, 48 h, 40 µM

Effects of Capsaicin Analogs on BGO1v

Fig. 8A

Untreated controls

JC011, 12.5µg/ml
3 h incubation

METHOD FOR REMOVING UNDIFFERENTIATED AND DEDIFFERENTIATED STEM CELL

CROSS-REFERENCE TO RELATED APPLICATION

This application is a National Phase Patent Application and claims the priority of International Application Number PCT/SG2010/000221, filed on Jun. 11, 2010, which claims priority to and the benefit of U.S. Provisional Patent Application No. 61/186,762, filed on Jun. 12, 2009.

TECHNICAL FIELD

The present invention generally relates to the use of compounds, including capsaicin analogues and derivatives thereof, for selectively removing undifferentiated stem cells or dedifferentiated stem cells from differentiated cells. The present invention also relates to compositions comprising differentiated cells, in which undifferentiated or dedifferentiated stem cells have been removed, and methods for their use.

BACKGROUND

Stem cells are cells that are capable of self-renewal through mitotic cell division, and differentiation into a diverse range of specialized cell types. Hence, stem cells hold considerable promise for use in human therapy, for example in regenerative medicine and tissue replacement after injury or disease. Existing stem cell therapies include bone marrow transplants that are used to treat leukemia, while future uses of stem cell therapy are envisaged in the treatment of other cancers, Parkinson's disease, spinal cord injuries, amyotrophic lateral sclerosis, multiple sclerosis, and muscle damage.

Various types of stem cells are known. Embryonic stem cells (ESC) are derived from embryonic tissue, typically from the epiblast tissue of the inner cell mass (ICM) of a blastocyst or earlier morula stage embryos. Embryonic stem cells are pluripotent. Hence, during development, ESCs are capable of giving rise to all derivatives of the three primary germ layers (the ectoderm, endoderm and mesoderm) and develop into each of the various cell types of the adult body when provided with the requisite stimulus for a particular cell type. The pluripotency of ESCs is due to a core regulatory network of transcription factors (including OCT-4, Nanog and SOX2) that ensures the suppression of genes leading to differentiation. If injected into the human body without providing the specific signals for correct differentiation into the correct cell type, the ESCs will differentiate into many different cell types and cause teratoma.

Another type of stem cell is induced pluripotent stem cell (IPSC). IPSCs are a type of pluripotent stem cells that are artificially derived from a non-pluripotent cell, for example an adult somatic cell, by inducing expression of certain genes. It is believed that IPSCs are identical to natural pluripotent stem cells, such as ESCs, in many aspects including the expression of certain stem cell genes and proteins, chromatin methylation patterns, doubling time, embryoid body formation, teratoma formation, viable chimera formation, potency and differentiability. Typically, IPSCs are produced by transfection of certain stem cell-associated genes (for example OCT-3/4 and SOX2) into non-pluripotent cells through the use of viral vectors, such as retroviruses.

Yet another type of stem cell is cancer stem cell (CSC). CSCs are found within tumors or hematological cancers, and have characteristics associated with normal stem cells, specifically the ability to undergo self-renewal and differentiate into a diverse range of cell types. However, the tight metabolic control under which normal stem cells divide is lost in CSCs. Hence, CSCs are tumorigenic (tumor-forming), and are believed to persist in tumors as a distinct population causing relapse and metastasis by giving rise to new tumors. CSCs are also known to be resistant to apoptosis and chemotherapy, the latter due to the presence of ATP-binding cassette transporters, which remove drugs from the cell.

In cell therapy, the self-renewal and pluripotent properties of stem cells such as ESCs and IPSCs are useful in providing specific types of differentiated cells that are transplanted into a patient in order to treat a particular disease or injury. However, the self-renewal property of such stem cells is also associated with tumorigenicity. Hence, while the differentiated cells that are transplanted into the patient are not known to be tumorigenic, there is a risk of transplantation of residual populations of undifferentiated stem cells that can result in teratoma formation and functional failure of the graft. Attempts to address this problem include the generation of ESCs that express a suicide gene that renders cells sensitive to administration of the anti-viral drug ganciclovir. However, such a strategy eliminates all cells of the graft in response to ganciclovir, which not only negates any benefit from the transplant procedure, but also results in additional intervention being necessary.

Furthermore, differentiated cells can potentially undergo dedifferentiation post-transplantation. Dedifferentiation is a cellular process where a partially or terminally differentiated cell reverts to an undifferentiated state.

There is a need to provide compounds, compositions and methods that overcome or at least ameliorate one or more of the disadvantages described above.

There is a need to provide compounds, compositions and methods for use in cell therapy, particularly to prevent teratoma formation.

There is a need to provide compounds, compositions and methods that selectively remove undifferentiated or dedifferentiated stem cells prior to or post transplantation in cell therapy.

There is a need to provide compounds, compositions and methods that specifically remove CSCs to treat and improve survival and quality of life of cancer patients, particularly patients suffering from metastatic forms of cancer.

There is a need to provide compounds that selectively remove undifferentiated or dedifferentiated stem cells, and that can be produced in large quantities in a simple and cost-effective manner.

SUMMARY

According to a first aspect, there is provided a use of a compound represented by the general formula (I):

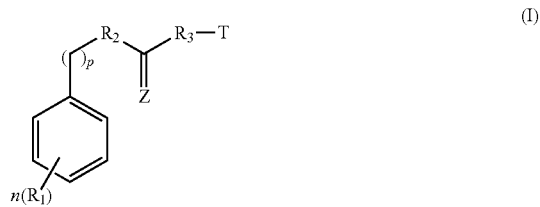

or a pharmaceutically acceptable salt thereof, wherein n is an integer from 2 to 5;

p is an integer from 0 to 4;

$R_1$ is independently selected from the group consisting of a hydroxyl group, an alkoxy group, a thiol group, a thioether group and an amino group, wherein at least two of $R_1$ is a hydroxyl group, a thiol group or an amino group, with the proviso that wherein n is 2, $R_1$ is not on the carbon-2 position and the carbon-5 position of the phenyl group;

$R_2$ and $R_3$ are independently a methylene group or a nucleophile, with the proviso that at least one of $R_2$ and $R_3$ is a nucleophile group;

Z is an oxygen (O) atom or sulfur (S) atom;

T is hydrogen or an optionally substituted aliphatic group;

in the manufacture of a medicament for treating a patient in need of cell therapy.

According to a second aspect, there is provided a method for removing undifferentiated stem cells or dedifferentiated stem cells from a sample comprising the cells, the method comprising administering to the cell sample an effective amount of a compound of the formula (I), or a pharmaceutically-acceptable salt thereof, as defined herein.

According to a third aspect, there is provided a method for preparing differentiated cells, the method comprising the steps of:

(a) removing undifferentiated stem cells or dedifferentiated stem cells from a cell population that comprises differentiated cells, and undifferentiated stem cells or dedifferentiated stem cells, by administering to the cell population an effective amount of a compound of the formula (I), or a pharmaceutically-acceptable salt thereof, as defined herein; and (b) culturing the remaining differentiated cells.

According to a fourth aspect, there is provided a pharmaceutical composition comprising a population of differentiated cells from which undifferentiated stem cells or dedifferentiated stem cells have been removed by the method of the second aspect.

According to a fifth aspect, there is provided a pharmaceutical composition comprising differentiated cells prepared according to the method of the third aspect, and a pharmaceutically acceptable carrier.

According to a sixth aspect, there is provided a method for the treatment of a patient in need of cell therapy, the method comprising administering to the patient an effective amount of a compound of the formula (I), or a pharmaceutically-acceptable salt thereof, as defined herein, or a pharmaceutical composition according to the fourth or fifth aspect.

According to a seventh aspect, there is provided a compound of the formula (I), or a pharmaceutically-acceptable salt thereof, as defined herein, for use in treating a patient in need of cell therapy.

According to an eighth aspect, there is provided a method for preventing dedifferentiation of differentiated cells, which comprises administering an effective amount of a compound of the formula (I), or a pharmaceutically-acceptable salt thereof, as defined herein, or a pharmaceutical composition according to the fourth or fifth aspect.

According to a ninth aspect, there is provided a method of enriching for a population of differentiated cells from a cell population comprising differentiated cells, undifferentiated stem cells or dedifferentiated stem cells, the method comprising the step of contacting the cell population with an effective amount of a compound of the formula (I) or a pharmaceutically-acceptable salt thereof as defined herein.

DEFINITIONS

The following words and terms used herein shall have the meaning indicated:

The term "stem cell" refers to an undifferentiated cell or a dedifferentiated cell that can give rise to at least one differentiated cell type through one or more cell division cycles. A stem cell is capable of self-renewal as well as proliferating, under appropriate conditions, to form progeny cells of more than one different phenotype and retaining this multi-lineage potential over time.

Included in the definition of "stem cells" are progenitor cells and embryonic stem cells (ESCs) that may be derived from pre-embryonic, embryonic or fetal tissue at any time after fertilization. Exemplary ESCs are human embryonic stem cells (hESCs); embryonic stem cells from other primates, such as Rhesus stem cells and marmoset stem cells; and human embryonic germ (hEG) cells, and the like. Other types of stem cells are also included in the term, such as any cells of primate origin that are capable of producing progeny cells of more than one different phenotype regardless of whether they were derived from pre-embryonic tissue, embryonic tissue, fetal tissue, or other sources such as malignant sources. Such other types of stem cells therefore include, but are not limited to, induced pluripotent stem cells (IPSCs) and cancer stem cells (CSCs).

IPSCs are believed to resemble natural pluripotent stem cells, such as ESCs, in many aspects, such as the expression of certain stem cell genes and proteins, chromatin methylation patterns, doubling time, embryoid body formation, teratoma formation, viable chimera formation, and potency and differentiability. For example, IPSCs have been shown to be morphologically similar to ESCs in that each cell has a round shape, a large nucleolus and scant cytoplasm. IPSCs have also been shown to be mitotically active, proliferating and dividing at a rate equal to ESCs, as well as capable of differentiating into fully differentiated tissues such as neurons and cardiomyocytes, and forming teratoma and embryoid bodies like ESCs. IPSCs have furthermore been shown to express cell surface antigenic markers expressed on ESCs, such as hESC-specific SSEA-3, SSEA-4, TRA-1-60, TRA-1-81, TRA-2-49/6E, and Nanog, as well as genes expressed in undifferentiated ESCs, such as Oct-3/4, Sox2, Nanog, GDF3, REX1, FGF4, ESG1, DPPA2, DPPA4, and hTERT.

The term "differentiation" and grammatical variants thereof refers to the process of acquiring individual characteristics that occurs during the progressive diversification of cells and tissues. As used herein, the terms "differentiated," "undifferentiated" and "dedifferentiated" are relative terms depending on the context in which they are used. When used with reference to cells, the term "undifferentiated" refers back to the same self-renewing stem cell; the term "dedifferentiated" refers to a cell that had formerly acquired a particular degree of differentiation, but has subsequently regained the ability to differentiate into one or more specialized cells (i.e. has become pluripotent or totipotent); and the term "differentiated" refers to one or more of the relatively mature cell phenotypes that the stem cell has diversified into.

Hence, as used herein, the terms "undifferentiated cells" and "dedifferentiated cells" refer to stem cells that have the ability to differentiate into cells of more than one different phenotype, while the term "differentiated cells" refers to cells that do not have this capability. "Undifferentiated stem cells," "dedifferentiated stem cells" and "differentiated cells" may be distinguishable by methods well known in the art. For example, cells may be distinguished based on, for example, morphology, their antigenic markers, and the gene transcripts they produce.

The term "enrich," when used herein in relation a cell culture or cell sample, refers to the increase in the concentration of a culture or sample component, or to the increase in the concentration of a culture or sample component of a culture or sample relative to other culture or sample components (which can be the result of reducing the concentration of other culture or sample components). For example, "enriching" differentiated cells from a cell culture or cell sample means increasing the proportion of differentiated cells to all cells in the cell culture or cell sample, that may contain a mixed population of undifferentiated stem cells, dedifferentiated stem cells and differentiated cells, amongst others. Alternatively, "enriching" differentiated cells from a cell culture or cell sample may refer to increasing the concentration of differentiated cells in the cell culture or cell sample (for example, by reducing the culture or sample volume), or reducing the concentration of other cellular components of the cell culture or cell sample.

The terms "feeder cells" and "feeder layers" are used interchangeably herein, and refer to cells of one type that are co-cultured with cells of a second type, so as to provide an environment in which the cells of the second type can be maintained and perhaps, proliferate. The feeder cells can be from a different species than the cells of the second type, the maintenance and proliferation of which they are supporting. For example, certain types of stem cells can be supported by murine feeder cells such as primary mouse embryonic fibroblasts (MEFs), immortalized mouse embryonic fibroblasts, or human fibroblast-like cells differentiated from hESCs. A stem cell population is said to be "essentially free" of feeder cells if the cells have been grown through at least one round after splitting in which fresh feeder cells are not added to support the growth of the stem cells. Typically, cultures that are "essentially free" of feeder cells contain less than about 5% feeder cells, and more typically, less than about 4%, about 3%, about 2%, or about 1% feeder cells.

The term "remove," and grammatical variants thereof, when used in relation to undifferentiated stem cells or dedifferentiated stem cells, refer to the separation of such cells from other components of the original sample, or from components of the sample that are remaining after one or more processing steps. The other components of the original sample include other cells, for example differentiated cells.

The removal of a target cell may be by killing, inhibiting or depleting the target cell in the sample by any of a variety of biological, biochemical, or biophysical means. By "killing" a target cell, it is meant destroying cellular growth of these cells, including making any change to the cell by application of the compounds disclosed herein, that leads to or causes immediate or eventual death of the cell. By "inhibiting" or "depleting" a target cell, it is meant a reduction in the number, proportion, proliferation or proliferation rate of the target cell by a measurable amount, or to the prevention of their proliferation entirely. Hence, the removal may be partial or complete.

The removal of a target cell is "selective" in that the target cell is preferentially killed, inhibited or depleted.

The term "cytotoxic effect" refers to the removal of a target cell. A "cytotoxic agent" refers to an agent that has a cytotoxic effect on the target cell.

The term "cell population" generally refers to a group of cells, typically of a common type. Typically, the cells in a cell population are derived from a common progenitor, although the phrase is also applicable to heterogeneous cell populations.

The term "homogenous" when used in relation to a cell population refers to a cell population that contains more than about 50%, 60%, 70%, 80%, 85%, 86%, 87%, 88%, 89%, 90%, 91%, 92%, 93%, 94%, 95%, 96%, 97%, 98%, or 99% of the desired cell lineage.

The term "analogue" refers to a compound which comprises a chemically modified form of a specific compound or class thereof, and which maintains the chemical or biological activities that are characteristic of the specific compound and class. For example, the term "analogue" as used herein may be used to refer to a chemically modified form of a compound of formula (I) which maintains the selective cytotoxic properties of a compound of formula (I).

The term "derivative" refers to any salt, solvate or prodrug, e.g. ester, of a compound of the invention, which upon administration to a subject, is capable of providing (directly or indirectly) a compound of the invention, or an active metabolite or residue thereof. Preparation of such derivatives is routine to those skilled in the art without undue experimentation.

The term "active compound" in connection with the present invention is understood as meaning a compound as disclosed herein which is capable of causing a required therapeutic effect in a patient or subject, for example selective removal of undifferentiated or dedifferentiated stem cells, or prevention of dedifferentiation of differentiated cells.

The term "pharmaceutically acceptable salt" refers to those salts which retain the chemical or biological effectiveness and properties of the active compound, which are not otherwise undesirable. A thorough discussion of pharmaceutically acceptable salts is available in Remington's Pharmaceutical Sciences (Mack Pub. Co., N.J. 1991).

The term "optionally substituted" as used herein means the group to which this term refers may be unsubstituted, or may be substituted with one or more groups independently selected from hydrogen, oxygen, sulfur, alkyl, alkenyl, alkynyl, thioalkyl, cycloalkyl, cycloalkenyl, heterocycloalkyl, halo, carboxyl, haloalkyl, haloalkynyl, hydroxyl, alkoxy, thioalkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, acylthio, phosphorus-containing groups such as phosphonyl and phosphinyl, aryl, heteroaryl, alkylaryl, alkylheteroaryl, cyano, cyanate, isocyanate, —C(O)NH(alkyl), and —C(O)N(alkyl)$_2$.

The term "hydroxyl" as used herein refers to the functional group —OH.

The term "alkoxy" as used herein refers to straight chain or branched alkyloxy groups. Examples include methoxy, ethoxy, n-propoxy, isopropoxy, tert-butoxy, and the like.

The term "thiol" means —SH.

The term "thioether" refers to ether groups wherein the oxygen is replaced with sulfur. The thioether groups include but are not limited to -alkylene-S-alkyl, -alkylene-S-aryl, -alkylene-S-arylalkyl, -alkylene-S-alkylaryl, -aryl-S-alkyl, -aryl-S-aryl, -aryl-S-alkylaryl, -aryl-S-arylalkyl, -arylalkyl-S-alkyl, -arylalkyl-S-aryl, -arylalkyl-S-alkylaryl, -arylalkyl-S-arylalkyl, -alkylaryl-S-alkyl, -alkylaryl-S-aryl, -alkylaryl-S-alkylaryl, and -alkylaryl-S-arylalkyl. The thioether groups may be optionally substituted as described herein.

The term "nucleophile" as used herein refers to a chemical moiety that has a reactive pair of electrons and that participates in a chemical reaction by donating electrons, i.e., nucleophiles are electron donor compounds. The nucleophile may be a halogen, nitrogen, sulfur or oxygen nucleophile. Exemplary nucleophiles include fluorides, cyanides, iodides, chlorides, bromides, acetates, enolates, primary amines, secondary amines, amino, alkoxides, thiols, alkyl sulfides (such as mercaptans), hydroxides, azides, and hydrazines, among others.

The term "amino" as used herein refers to groups of the form —NR$_a$ or —NR$_a$R$_b$ wherein R$_a$ and R$_b$ are independently selected from the group including but not limited to hydrogen, optionally substituted alkyl, optionally substituted alkenyl, optionally substituted alkynyl, optionally substituted alkoxy and optionally substituted aryl groups. For example, the term "amino" as used herein may be used to refer to an —NH group at the R$_2$ and/or R$_3$ position of a compound of formula (I), or to an —NHCH$_3$ group in the optionally substituted aliphatic group at the T position of a compound of formula (I).

The term "aliphatic" refers to a linear, branched, or cyclic alkyl, alkenyl, or alkynyl group.

The term "alkyl" includes within its meaning straight chain or branched chain saturated aliphatic groups having from 1 to 30 carbon atoms, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms. For example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, decyl, and the like.

The term "lower alkyl" refers to a straight or branched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-pentyl, n-hexyl, and the like.

The term "alkenyl" includes within its meaning straight or branched chain unsaturated aliphatic hydrocarbon groups having from 2 to 30 carbon atoms, e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms and having at least one double bond, of either E, Z, cis or trans stereochemistry where applicable, anywhere in the alkyl chain. Examples of alkenyl groups include but are not limited to ethenyl, vinyl, allyl, 1-methylvinyl, 1-propenyl, 2-propenyl, 2-methyl-1-propenyl, 2-methyl-1-propenyl, 1-butenyl, 2-butenyl, 3-butenyl, 1,3-butadienyl, 1-pentenyl, 2-pentenyl, 3-pentenyl, 4-pentenyl, 1,3-pentadienyl, 2,4-pentadienyl, 1,4-pentadienyl, 3-methyl-2-butenyl, 1-hexenyl, 2-hexenyl, 3-hexenyl, 1,3-hexadienyl, 1,4-hexadienyl, 2-methylpentenyl, 1-heptenyl, 2-heptenyl, 3-heptenyl, 1-octenyl, 1-nonenyl, 1-decenyl, and the like.

The term "lower alkenyl" refers to a straight or branched saturated hydrocarbon chain having 2, 3, 4, 5, or 6 carbon atoms.

The term "alkynyl" as used herein includes within its meaning straight or branched chain unsaturated aliphatic hydrocarbon groups having from 2 to 30 carbon atoms and having at least one triple bond anywhere in the carbon chain. Examples of alkynyl groups include but are not limited to ethynyl, 1-propynyl, 1-butynyl, 2-butynyl, 1-methyl-2-butynyl, 3-methyl-1-butynyl, 1-pentynyl, 1-hexynyl, 1-methylpentynyl, 1-heptynyl, 2-heptynyl, 1-octynyl, 2-octynyl, 1-nonyl, 1-decynyl, and the like.

The term "lower alkynyl" refers to a straight or branched saturated hydrocarbon chain having 2, 3, 4, 5, or 6 carbon atoms.

The term "heteroatom" or variants such as "hetero-" as used herein refers to oxygen (O), nitrogen (N), phosphorus (P) and sulfur (S).

The term "aryl" or variants such as "aromatic group" or "arylene" as used herein refers to single, polynuclear, conjugated and fused residues of aromatic hydrocarbons typically having from 6 to 14 carbon atoms. Exemplary aryl groups include, but are not limited to phenyl, naphthyl, tetrahydronaphthyl, and the like.

The term "heteroaryl" and variants such as "heteroaromatic group" or "heteroarylene" as used herein, includes within its meaning single, polynuclear, conjugated and fused aromatic moieties having 5 to 20 atoms wherein 1 to 6 atoms are heteroatoms selected from O, N, NH and S. Examples of such groups include pyridyl, 2,2'-bipyridyl, phenanthrolinyl, quinolinyl, thiophenyl, indoyl, furanyl and pyrrolyl moieties and the like.

The term "cycloalkyl" as used herein refers to cyclic saturated aliphatic groups and includes within its meaning monocyclic, bicyclic, polycyclic or fused polycyclic hydrocarbon moieties having from 3 to 10 carbon atoms, e.g., 3, 4, 5, 6, 7, 8, 9, or 10 carbon atoms. Examples of cycloalkyl groups include but are not limited to cyclopropyl, 2-methylcyclopropyl, cyclobutyl, cyclopentyl, 2-methylcyclopentyl, 3-methylcyclopentyl, cyclohexyl, and the like.

The term "halide" or variants such as "halogen" or "halo" as used herein refers to fluoride, chloride, bromide and iodide.

The present invention includes within its scope all isomeric forms of the compounds disclosed herein, including all diastereomeric isomers, racemates and enantiomers. Thus, compounds of formula (I) and derivatives thereof should be understood to include, for example, E, Z, cis, trans, (R), (S), (L), (D), (+), and/or (−) forms of the compounds, as appropriate in each case.

The term "treatment" includes any and all uses which remedy a disease state or symptoms, prevent the establishment of disease, or otherwise prevent, hinder, retard, or reverse the progression of disease or other undesirable symptoms in any way whatsoever. Hence, "treatment" includes prophylactic and therapeutic treatment. For purposes of this invention, beneficial or desired clinical results include, but are not limited to, alleviation of symptoms; diminishment of extent of condition, disorder or disease; stabilized (i.e., not worsening) state of condition, disorder or disease; delay or slowing of condition, disorder or disease progression; amelioration of the condition, disorder or disease state, remission (whether partial or total), whether detectable or undetectable; or enhancement or improvement of condition, disorder or disease. Treatment includes eliciting a cellular response that is clinically significant, without excessive levels of side effects. Treatment also includes prolonging survival as compared to expected survival if not receiving treatment.

The term "patient" or "subject" refers to patients or subjects of human or other mammal and includes any individual it is desired to examine or treat using the active compounds, compositions and methods disclosed herein. However, it will be understood that "patient" or "subject" does not imply that symptoms are present. Suitable mammals that fall within the scope of the invention include, but are not restricted to, primates, livestock animals (eg. sheep, cows, horses, donkeys, pigs), laboratory test animals (e.g. rabbits, mice, rats, guinea pigs, hamsters), companion animals (e.g. cats, dogs) and captive wild animals (e.g. foxes, deer, dingoes). "Mammal" refers to any animal classified as a mammal, including humans, domestic and farm animals, and zoo, sports, and pet companion animals such as a household pet and other domesticated animal such as, but not limited to, cattle, sheep, ferrets, swine, horses, poultry, rabbits, goats, dogs, cats and the like. Preferred companion animals are dogs and cats. Preferably, the mammal is human.

The term "cell therapy" refers to the injection, transplantation or placement by any other means, of cells or other cellular materials, into a patient or subject to replace or repair damaged tissue or cells. The cells may be autologous, modified (for example genetically, chemically, biochemically, physically etc.), or regenerative cells. The cells may produce a protein.

The term "administering" and variations of that term including "administer" and "administration", includes contacting, applying, delivering or providing a compound or composition of the invention to an organism, or a surface by any appropriate means.

The term "effective amount" when used in relation to an active compound, refers to an amount sufficient to effect the desired therapeutic benefit. Similarly, the terms "therapeutically effective amount" and "pharmaceutically effective amount" include within their meanings a sufficient but non-toxic amount of a compound or composition of the invention to provide the desired therapeutic or prophylactic effect. The exact amount required will vary from subject to subject depending on factors such as the species being treated, the age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

The term "dosage unit form" as used herein refers to physically discrete units suited as unitary dosages for the individual to be treated; each unit containing a predetermined quantity of compound(s) is calculated to produce the desired therapeutic effect in association with the required pharmaceutical carrier. The compound(s) may be formulated for convenient and effective administration in effective amounts with a suitable pharmaceutically acceptable carrier in an acceptable dosage unit. In the case of compositions containing supplementary active ingredients, the dosages are determined by reference to the usual dose and manner of administration of the ingredients.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

The term "or" as used herein is to be interpreted as an inclusive, or meaning any one, or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Exemplary, non-limiting embodiments of capsaicin analogues and their use as cytotoxic agents to selectively remove undifferentiated or dedifferentiated stem cells from differentiated cells will now be disclosed.

Active Compounds

The active compounds may be represented by a compound having the general formula (I):

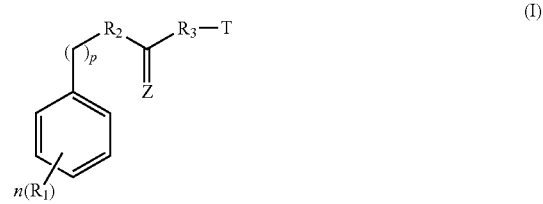

and pharmaceutically acceptable salts thereof, wherein
n is an integer from 2 to 5;
p is an integer from 0 to 4;
$R_1$ is selected from the group consisting of a hydroxyl group, an alkoxy group, a thiol group, a thioether group and an amino group, wherein at least two of $R_1$ is a hydroxyl group, a thiol group or an amino group, with the proviso that wherein n is 2, $R_1$ is not on the carbon-2 position and the carbon-5 position of the phenyl group;
$R_2$ and $R_3$ are independently a methylene group or a nucleophile, with the proviso that at least one of $R_2$ and $R_3$ is a nucleophile group;
Z is an oxygen (O) atom or sulfur (S) atom;
T is hydrogen or an optionally substituted aliphatic group.
In one embodiment, n is 2.
In one embodiment, Z is an oxygen (O) atom.
In one embodiment, Z is not a sulfur (S) atom.
In one embodiment wherein n is 2, $R_1$ is on the carbon-3 position and the carbon-4 position of the phenyl group.
In one embodiment where n is 2, each of $R_1$ is —OH. Preferably, in embodiments where n is 2 and each of $R_1$ is —OH, one of $R_1$ is on the carbon-3 position and the other $R_1$ is on the carbon-4 position of the phenyl group.
In one embodiment, Z is an oxygen (O) atom, n is 2, and each of $R_1$ is —OH.
In one embodiment, Z is not a sulfur (S) atom, n is 2, and each of $R_1$ is —OH.

In a preferred embodiment wherein n is 2, one of $R_1$ is a hydroxyl group and the other of $R_1$ is an amino group. In a more preferred embodiment wherein n is 2, one of $R_1$ is a hydroxyl and the other of $R_1$ is a thiol group. In a most preferred embodiment wherein n is 2, both of $R_1$ is a hydroxyl group.

In another embodiment wherein n is 2, one of $R_1$ is a thiol group and the other of $R_1$ is an amino group. In other embodiments wherein n is 2, both of $R_1$ is a thiol group or both of $R_1$ is an amino group.

p can be 0, 1, 2, 3 or 4. In one embodiment, p is 1.

In one embodiment, n is 3 to 5 and the remaining $R_1$ is OU, wherein U is an alkyl group having from 1 to 6 carbon atoms.

In another embodiment, n is 3 to 5 and the remaining $R_1$ is $Z_1T_1$, wherein $Z_1$ is a sulfur (S) atom or oxygen (O) atom and $T_1$ is a hydrogen or a lower alkyl group. The lower alkyl preferably has from 1 to 6 carbon atoms.

In embodiments where n is 3 to 5, the remaining $R_1$ is independently selected from the group consisting of —OH, —OCH$_3$, OCH$_2$CH$_3$, OCH$_2$CH$_2$CH$_3$, OCH$_2$CH$_2$CH$_2$CH$_3$, OCH$_2$CH$_2$CH$_2$CH$_2$CH$_3$, OCH$_2$CH$_2$CH$_2$CH$_2$CH$_2$CH$_3$, —SH, —SCH$_3$, —SCH$_2$CH$_3$, —SCH$_2$CH$_2$CH$_3$, —SCH$_2$CH$_2$CH$_2$CH$_3$, —SCH$_2$CH$_2$CH$_2$CH$_2$CH$_3$ and —SCH$_2$CH$_2$CH$_2$CH$_2$CH$_2$CH$_3$.

In some embodiments where n is 2, 3, 4 or 5, all the $R_1$ groups are the same. For example, where n is 2, both $R_1$ groups may be hydroxyl groups, both. $R_1$ groups may be thiol groups, or both $R_1$ groups may be amino groups. Similarly, where n is 3, all three $R_1$ groups may be hydroxyl groups, all three $R_1$ groups may be thiol groups, or all three $R_1$ groups may be amino groups; and where n is 4, all four $R_1$ groups may be hydroxyl groups, all four $R_1$ groups may be thiol groups, or all four $R_1$ groups may be amino groups.

In other embodiments where n is 2, 3, 4 or 5, each $R_1$ group is different. For example, where n is 2, one $R_1$ group may be a hydroxyl group and the other $R_1$ group may be a thiol group, or one $R_1$ group may be a hydroxyl group and the other $R_1$ group may be an amino group, or one $R_1$ group may be a thiol group and the other $R_1$ group may be an amino group. Similarly, where n is 3, the first $R_1$ group may be a hydroxyl group, the second $R_1$ group may be a thiol group and the third $R_1$ group may be —OCH$_3$; or the first $R_1$ group may be a hydroxyl group, the second $R_1$ group may be an amino group and the third $R_1$ group may be —OCH$_2$CH$_2$CH$_3$; or the first $R_1$ group may be a thiol group, the second $R_1$ group may be an amino group and the third $R_1$ group may be a thioether group; or the first and second $R_1$ groups may be hydroxyl groups and the third $R_1$ group may be —OCH$_2$CH$_2$CH$_3$; or the first and second $R_1$ groups may be thiol groups and the third $R_1$ group may be a thioether.

In one embodiment, T is an aliphatic group with 1 to 30 carbons. Preferably, T is an aliphatic group with 1 to 20 carbons. More preferably, T is an aliphatic group with 1 to 15 carbons. Most preferably, T is an aliphatic group with 5 to 15 carbons.

In one embodiment, T is an aliphatic group with 1 to 15 carbons. In another embodiment, T is an aliphatic group with 1 to 14 carbons. In another embodiment, T is an aliphatic group with 1 to 13 carbons. In another embodiment, T is an aliphatic group with 1 to 12 carbons. In another embodiment, T is an aliphatic group with 1 to 11 carbons. In another embodiment, T is an aliphatic group with 1 to 10 carbons. In another embodiment, T is an aliphatic group with 1 to 9 carbons. In another embodiment, T is an aliphatic group with 1 to 8 carbons. In another embodiment, T is an aliphatic group with 1 to 7 carbons. In another embodiment, T is an aliphatic group with 1 to 6 carbons. In another embodiment, T is an aliphatic group with 1 to 5 carbons, 1 to 4 carbons, 1 to 3 carbons, or 1 to 2 carbons.

In one embodiment, the aliphatic group of T is an alkyl, preferably a lower alkyl. The alkyl may be straight chain alkyl or branched chain alkyl. Preferably, the alkyl is a straight chain alkyl. The alkyl may be —CH$_3$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, CH$_2$CH$_2$CH$_2$CH$_2$CH$_2$CH$_2$CH$_3$, —CH$_2$CH$_2$CH$_2$CH$_2$CH$_2$CH$_2$CH$_2$CH$_3$, —CH$_2$CH$_2$CH$_2$CH$_2$CH$_2$CH$_2$CH$_2$CH$_2$CH$_3$ or —CH(CH$_3$)$_2$.

In one embodiment, the aliphatic group of T is an aliphatic group containing at least one unsaturated alkenyl or alkynyl group, preferably lower alkenyl or lower alkynyl groups. Suitable alkenyl groups include —CHCH$_2$, —CH$_2$CHCH$_2$, and —CHCHCH$_3$, while suitable alkynyl groups include —CCCH$_3$, —CH$_2$CCH, —CH$_2$CH$_2$CCH, —CH$_2$CH$_2$CH$_2$CCH, —CH$_2$CH$_2$CH$_2$CH$_2$CCH, and —CH$_2$CCCH$_3$.

In another embodiment, T is an aliphatic group substituted with one or more heteroatom groups. Suitable heteroatom groups include, without limitation, oxygen (O), sulfur (S), and nitrogen (N) and phosphorous (P).

In yet another embodiment, T is an aryl group, heteroaryl group or cycloalkyl group, each optionally substituted with one or more groups selected from hydrogen, oxygen, sulfur, alkyl, alkenyl, alkynyl, thioalkyl, cycloalkyl, cycloalkenyl, heterocycloalkyl, halo, carboxyl, haloalkyl, haloalkynyl, hydroxyl, alkoxy, thioalkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, acylthio, phosphonyl, phosphinyl, aryl, heteroaryl, alkylaryl, alkylheteroaryl, cyano, cyanate, isocyanate, —C(O)NH(alkyl), and —C(O)N(alkyl).

In one embodiment, both $R_2$ and $R_3$ are methylene groups. In another embodiment, one of $R_2$ and $R_3$ is a methylene group and the other is a nucleophile. In yet another embodiment, both $R_2$ and $R_3$ are nucleophiles.

In one embodiment, the nucleophile of $R_2$ and/or $R_3$ is selected from the group consisting of a halide, a nitrogen nucleophile, a sulfur nucleophile and an oxygen nucleophile.

Suitable halides include, but are not limited to, fluoride, chloride, bromide and iodide, and the like.

Suitable nitrogen nucleophiles include, but are not limited to, amino groups (e.g. primary amino groups, secondary amino groups and tertiary amino groups), and azides (e.g. metal azides of Li, Na or K), and the like.

Suitable sulfur nucleophiles include thiols and alkyl sulfides, and the like.

Suitable oxygen nucleophiles include acetates, enolates, alkoxides, and hydroxides, and the like.

The halide, nitrogen nucleophile, sulfur nucleophile and oxygen nucleophile may be optionally substituted as described herein.

In one embodiment of the compounds described herein, the nucleophile of $R_2$ and/or $R_3$ is a nitrogen nucleophile.

In one embodiment, the nitrogen nucleophile is an amino group. The amino group may be a NH group, a NHV group or a NVV' group where V and V' are each independently selected from the group consisting of a $C_1$-$C_6$ lower alkyl, a phenyl, and an alkoxy group.

In a preferred embodiment of the compounds described herein, $R_2$ is a nucleophile and $R_3$ is a methylene group. In a more preferred embodiment of the compounds described herein, $R_2$ is a nitrogen nucleophile and $R_3$ is a methylene group. In a most preferred embodiment of the compounds described herein, $R_2$ is a NH group and $R_3$ is a methylene group.

In one embodiment, the compound is selected from the group consisting of:

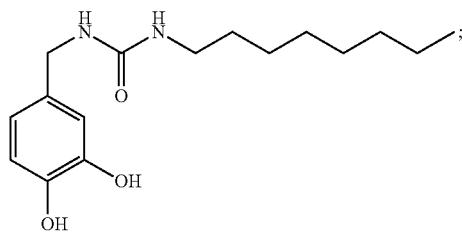
(II)

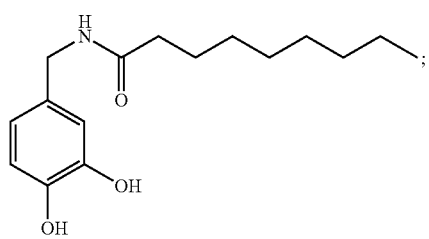
(III)

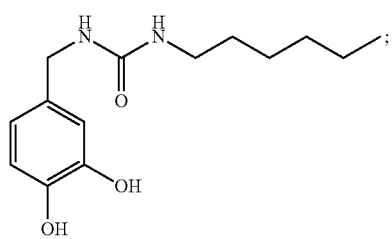
(IV)

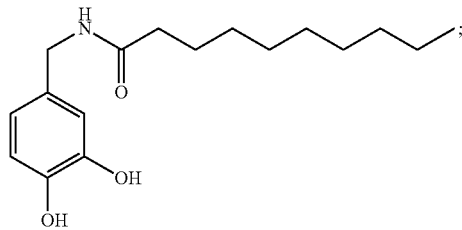
(V)

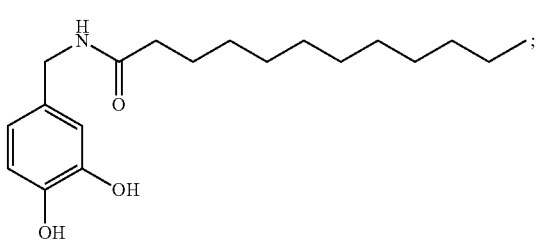
(VI)

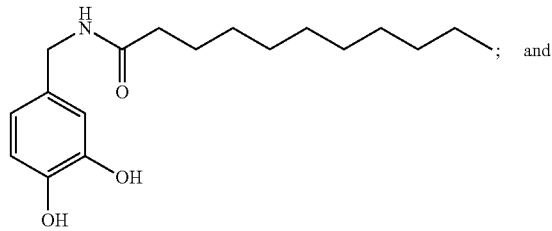
(VII)

; and

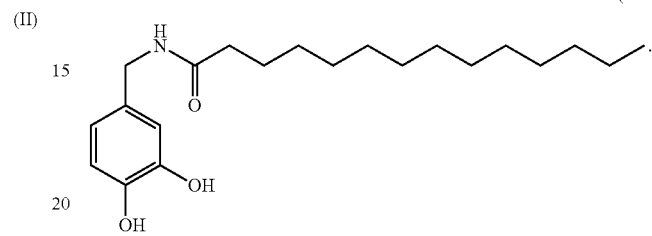
(VIII)

In a preferred embodiment, the compound has the formula (II):

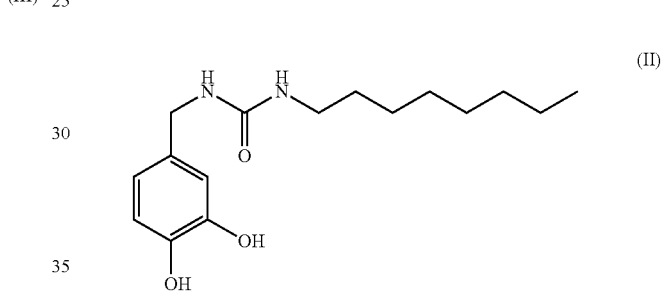
(II)

In another preferred embodiment, the compound has the formula (III):

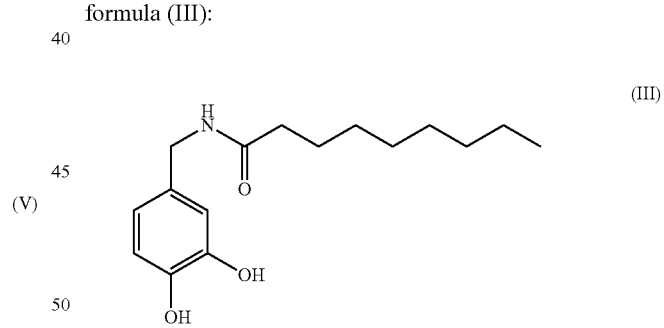
(III)

In another preferred embodiment, the compound has the formula (IV):

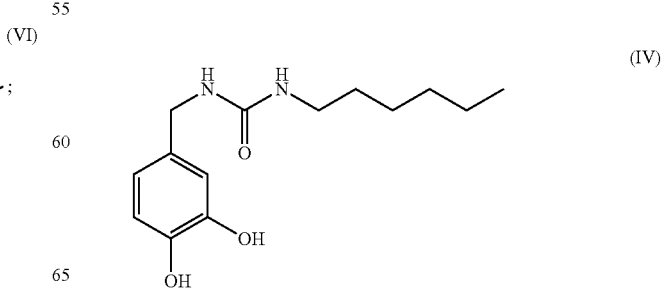
(IV)

In another preferred embodiment, the compound has the formula (V):

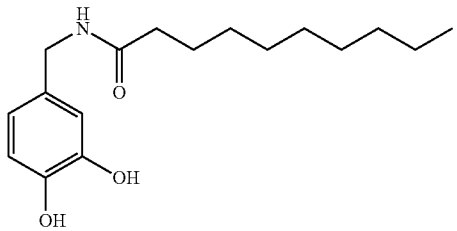 [SMILES: CCCCCCCCCC(=O)NCc1ccc(O)c(O)c1]
(V)

In another preferred embodiment, the compound has the formula (VI):

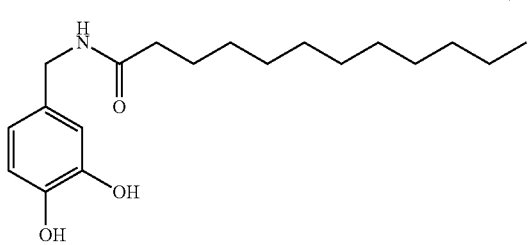 [SMILES: CCCCCCCCCCCC(=O)NCc1ccc(O)c(O)c1]
(VI)

In another preferred embodiment, the compound has the formula (VII):

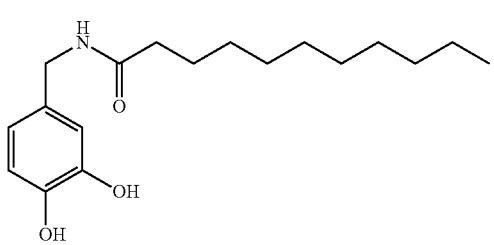 [SMILES: CCCCCCCCCCC(=O)NCc1ccc(O)c(O)c1]
(VII)

In another preferred embodiment, the compound has the formula (VIII):

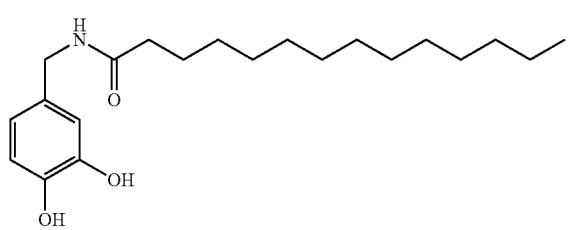 [SMILES: CCCCCCCCCCCCCC(=O)NCc1ccc(O)c(O)c1]
(VIII)

Synthesis of Active Compounds

The disclosed active compounds having the general formula (I) may be prepared by a process as described below.

Generally, the active compounds are synthesized via nucleophilic substitution reactions. A nucleophile and a second reactant are mixed in an anhydrous solvent, and stirred at room temperature to produce the active compounds. The active compounds are extracted with an organic solvent, and the resulting organic extracts are concentrated under reduced pressure to give a crude product.

The nucleophile is an amine having a formula (Ia), or a hydrochloride or hydrobromide salt thereof having a formula (Ia') as shown below:

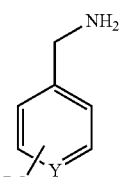
(Ia)

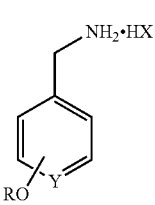
(Ia')

where R is H or $CH_3$, Y is N or CH, and X is Cl or Br.

Preferably, the nucleophile is a hydrochloride or hydrobromide salt of the amine having a formula (Ia'). The R group of the salt is preferably a hydrogen (H).

Alternatively, the nucleophile is a straight chain amine having a formula (Ia"):

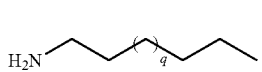
(Ia")

where q is 1 or 3.

The second reactant is an acid chloride (such as a nonanoyl chloride), an isocyanate or isothiocyanate, or a lactone.

The nucleophile and the second reactant are typically used in a stoichiometric ratio, but the excess of one component or the other may be advantageous.

The anhydrous solvent is N,N-dimethylformamide (DMF), dichloromethane or tetrahydrofuran.

Where the nucleophile used is a hydrochloride or hydrobromide salt of an amine having a formula (Ia'), N,N-diisopropylethylamine (DIPEA) can be added to liberate the amine group.

Where the second reactant used is a lactone, 2-hydroxypyridine is added as a reaction catalyst.

Typically, the mixture, is stirred at room temperature for 6 to 24 h before being extracted with an organic solvent such as dichloromethane. The organic extract is concentrated under reduced pressure to give a crude active compound, which is then purified using silica gel column chromatography or preparative high performance liquid chromatography.

Active Compound Salts

In some forms, it may be desirable to formulate the active compounds in a pharmaceutically acceptable salt form, generally to improve the solubility and bioavailability and to provide an active compound that may be capable of being assimilated readily. Preferably, the pharmaceutically acceptable salts are suitable for use in contact with the tissues of humans and animals without undue toxicity, irritation, allergic response and the like, and are commensurate with a reasonable benefit/risk ratio.

The active compounds may form pharmaceutically acceptable salts with both organic and inorganic acids. Suitable physiologically tolerated acids for salt formation may be organic and inorganic acids, such as hydrochloric, sulfuric, phosphoric, acetic, citric, oxalic, malonic, salicylic, malic, fumaric, succinic, ascorbic, maleic, methanesulfonic, isethionic, lactic, gluconic, glucuronic, sulfamic, benzoic, tartaric, pamoic, and the like.

The salts may be prepared by contacting a free base form with an equivalent amount of the desired acid in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions may be suitable for this purpose.

The free base forms may differ from their respective salt forms somewhat in certain physical properties such as solubility in polar solvent. Otherwise, the salts may be equivalent to their respective free base forms for purposes of the invention.

The active compounds may exist in unsolvated as well as solvated forms, including hydrated forms. Such salt forms of the active compound may be provided or mixed prior to use with a physiologically acceptable solvent such as water or ethanol.

Use of Active Compounds in Cell Therapy

In one embodiment, the active compounds disclosed herein are used for treating a patient in need of cell therapy. The active compounds disclosed herein may be used as selective cytotoxic agents in cell therapy. The active compounds may be used to selectively remove a target cell, or a population of the target cells, from a mixed population of cells in a sample. The selective removal of the target cell may be carried out in vivo, ex vivo or in vitro.

The sample may be biological samples such as tissues, cells, body fluids and isolates thereof etc., isolated from a subject (i.e. the sample is in vitro), as well as tissues, cells and fluids etc. present within a subject (i.e. the sample is in vivo). Examples of biological samples include: whole blood, blood fluids (e.g. serum and plasma), lymph and cystic fluids, sputum, stool, tears, mucus, hair, skin, ascitic fluid, cystic fluid, urine, nipple exudates, nipple aspirates, sections of tissues such as biopsy and autopsy samples, frozen sections taken for histologic purposes, archival samples, explants and primary or tissue cultures derived from patient tissues etc. A sample can also be obtained from cell or tissue culture. The sample may be untreated, treated, diluted or concentrated from a patient.

In one embodiment, the cell therapy requires removing undifferentiated stem cells from differentiated cells. The undifferentiated stem cells may be selected from the group consisting of human embryonic stem cells (hESCs), induced pluripotent stem cells (IPSCs) and cancer stem cells (CSCs).

In another embodiment, the cell therapy requires removing dedifferentiated stem cells from differentiated cells. The dedifferentiated stem cells may be selected from the group consisting of human embryonic stem cells (hESCs), induced pluripotent stem cells (IPSCs) and cancer stem cells (CSCs).

In one embodiment, the removing of the stem cells is in vivo, in vitro or ex vivo.

In one embodiment, the sample is a cell sample that comprises cells in culture (i.e. in vitro) that is to be transplanted into a patient in need of cell therapy. In another embodiment, the sample is a cell sample that comprises cells present within a patient who is in need of, or has undergone, cell therapy (i.e. in vivo). In a further embodiment, the sample is a cell sample that has been removed from the patient, treated with the active compounds or compositions thereof, and then transplanted back into the patient (i.e. ex vivo).

In one embodiment, a patient who is in need of cell therapy has a condition selected from the group consisting of cancer, autoimmune disease, proliferative disorder, inflammatory disorder, neurological disorder, age-related disorder, allergic disorder, immune disorder, viral infection, burn, trauma, other conditions involving tissue injury, and other conditions wherein cell therapy is desirable.

Autoimmune diseases include systemic lupus erythematosis, rheumatoid arthritis, Sjogren's syndrome, Reiter's syndrome, systemic sclerosis, polyarteritis nodosa, multiple sclerosis, juvenile oligoarthritis, collagen-induced arthritis, experimental autoimmune encephalomyelitis (EAE), inflammatory bowel disease (e.g. Crohn's disease, ulcerative colitis), autoimmune gastric atrophy, pemphigus vulgaris, psoriasis, vitiligo, type I diabetes, myasthenia gravis, Grave's disease, Hashimoto's thyroiditis, sclerosing sialadenitis, sclerosing cholangitis, Addison's disease, scleroderma, polymyositis, dermatomyositis, pernicious anemia, sympathetic ophthalmitis, and the like.

Proliferative disorders that may be treated using the compounds, compositions and methods disclosed herein include cell proliferative disorders such as blood vessel proliferative disorders, fibrotic disorders (e.g. scleroderma), angiogenesis, tumor growth, rheumatoid arthritis, age-related muscular degeneration, neoplastic disorders such as head and neck carcinomas and carcinomas of the regional lymph nodes including cervical lymph nodes, prelaryngeal lymph nodes, pulmonary juxtaesophageal lymph nodes and submandibular lymph nodes.

Other cancers that may be treated using the compounds, compositions and methods disclosed herein include breast cancer, gastric cancer, bladder cancer, ovarian cancer, thyroid cancer, lung cancer, prostate cancer, uterine cancer, testicular cancer, neuroblastoma, squamous cell carcinoma of the head, neck, cervix and vagina, multiple myeloma, soft tissue and osteogenic sarcoma, colorectal cancer, liver cancer (i.e. hepatocarcinoma), renal cancer (i.e. renal cell carcinoma), pleural cancer, pancreatic cancer, cervical cancer, anal cancer, bile duct cancer, gastrointestinal carcinoid tumors, esophageal cancer, gall bladder cancer, small intestine cancer, cancer of the central nervous system, skin cancer, choriocarcinoma, osteogenic sarcoma, fibrosarcoma, glioma, melanoma, B-cell lymphoma, non-Hodgkin's lymphoma, Burkitt's lymphoma, small cell lymphoma, large cell lymphoma, monocytic leukemia, myelogenous leukemia, acute lymphocytic leukemia, and acute myelocytic leukemia.

Neurological disorders are disorders that affect the central nervous system (e.g. brain, brainstem and cerebellum), the peripheral nervous system (peripheral nerves and cranial nerves included) and/or the autonomic nervous system (parts of which are located in both central and peripheral nervous system). Neurological disorders include, for example, neurodegenerative disorders (e.g. Parkinson's disease or Alzheimer's disease), behavioral disorders or neuro-psychiatric disorders (e.g. bipolar affective disorder or unipolar affective disorder or schizophrenia) and myelin-related disorders (e.g. multiple sclerosis).

Allergic disorders that may be treated using the compounds, compositions and methods disclosed herein include atopic dermatitis, atopic asthma, conjunctival allergy, allergic rhinitis, food allergy, urticaria, contact dermatitis, allergic reactions to drugs, and anaphylaxis.

Exemplary inflammatory disorders that may be treated using the compounds, compositions and methods disclosed herein include rheumatoid arthritis, Crohn's disease, mastocytosis, asthmas, multiple sclerosis, inflammatory bowel syndrome and allergic rhinitis.

Other examples of conditions that may be treated using the compounds, compositions and methods disclosed herein include lupus, diabetes, amyotrophic lateral sclerosis, Huntington's disease, paralysis, thyroiditis, AIDS, psoriatic arthritis, pancreatitis, hematologic malignancies, muscle damage, non-specific cell damage associated with radiotherapy or chemotherapy, cardiac injuries (e.g. associated with heart attack), and spinal cord injuries, amongst others.

Preferably, the removal of the target cell, or a population of the target cells, is by at least about 10% relative to a control. More preferably, the removal is by at least about 25%, about 50%, about 75% or about 85% relative to a control. Even more preferably, the removal is by at least about 95% relative to a control. Most preferably, the removal is complete, that is about 100% relative to a control. For example, the removal is by about 10% to about 100%, about 20% to about 100%, about 30% to about 100%, about 40% to about 100%, about 50% to about 100%, about 60% to about 100%, about 70% to about 100%, about 80% to about 100%, about 90% to about 100%, about 10% to about 90%, about 10% to about 80%, about 10% to about 70%, about 10% to about 60%, about 10% to about 50%, about 10% to about 40%, about 10% to about 30%, or about 10% to about 20%.

The mixed population of cells typically comprises a mixture of cells, including but not limited to undifferentiated stem cells, dedifferentiated stem cells and differentiated cells.

In one embodiment, the cell sample comprising the mixed population of cells is an undifferentiated stem cell sample. A cell sample may be described as an "undifferentiated" stem cell sample when a substantial proportion of the cells in the cell population are stem cells, or their derivatives, which display morphological characteristics of undifferentiated stem cells that clearly distinguish them from differentiated cells of embryo or adult origin. Typically, undifferentiated stem cells appear in the two dimensions of a microscopic view in colonies of cells with high nuclear/cytoplasmic ratios and prominent nucleoli, and are easily recognized by those skilled in the art. Typically, colonies of undifferentiated stem cells within the population will be surrounded by neighboring cells that are differentiated, but will persist when the population is cultured or passaged under appropriate conditions such that individual undifferentiated stem cells will constitute a substantial proportion of the cell population. Typically, cultures that are substantially undifferentiated contain at least about 20% undifferentiated stem cells, and more typically, contain at least about 40%, about 60%, or about 80% undifferentiated stem cells. For example, cultures that are substantially undifferentiated may contain about 20% to about 80%, about 20% to about 70%, about 20% to about 60%, about 20% to about 50%, about 20% to about 40%, about 20% to about 30%, about 30% to about 80%, about 40% to about 80%, about 50% to about 80%, about 60% to about 80%, or about 70% to about 80% undifferentiated stem cells.

In another embodiment, the cell sample comprising the mixed population of cells is a dedifferentiated stem cell sample. A cell sample may be described as a "dedifferentiated" stem cell sample when a substantial proportion of the cells in the cell population are stem cells, or their derivatives, which display characteristics of dedifferentiated stem cells that clearly distinguish them from differentiated cells of embryo or adult origin. Like undifferentiated stem cells, dedifferentiated stem cells which have reverted to a pluripotent phenotype, from a differentiated phenotype, can undergo differentiation into cells of more than one phenotype. Dedifferentiated stem cells may also be distinguished from differentiated cells based on the expression profiles of stem cell marker genes and proteins. Exemplary stem cell marker genes and proteins include, but are not limited to, UTF-1, GCTM-2, SSEA-3, SSEA-4, Tra-1-60, Tra-1-81, Oct4, Nanog, LIN-28, SOX2, ALDH, Bcl-2, c-kit, ECMA-7, Flk-2, GDF3, HAS2, IL-3Rα, KDR, Lrp4, MRP4, notch-1, Oct3, P-gp/MDR1, Rex-1, SOX9, SOX10, Thy-1, VEGFR-2, Zac1, and, the like. Typically, cultures that are substantially dedifferentiated contain at least about 20% dedifferentiated stem cells, and more typically, contain at least about 40%, about 60%, or about 80% dedifferentiated stem cells. For example, cultures that are substantially dedifferentiated may contain about 20% to about 80%, about 20% to about 70%, about 20% to about 60%, about 20% to about 50%, about 20% to about 40%, about 20% to about 30%, about 30% to about 80%, about 40% to about 80%, about 50% to about 80%, about 60% to about 80%, or about 70% to about 80% dedifferentiated stem cells.

In one embodiment, a cell sample is substantially an undifferentiated and dedifferentiated stem cell sample. For example, the cell sample may contain about 20% undifferentiated stem cells and about 20% dedifferentiated stem cells, or about 20% undifferentiated stem cells and about 40% dedifferentiated stem cells, or about 20% undifferentiated stem cells and about 60% dedifferentiated stem cells, or about 20% undifferentiated stem cells and about 80% dedifferentiated stem cells. Alternatively, the cell sample may contain about 20% dedifferentiated stem cells and about 40% undifferentiated stem cells, or about 20% dedifferentiated stem cells and about 60% undifferentiated stem cells, or about 20% dedifferentiated stem cells and about 80% undifferentiated stem cells.

In one embodiment, a cell sample contains undifferentiated stem cells but not dedifferentiated stem cells. In another embodiment, a cell sample contains dedifferentiated stem cells but not undifferentiated stem cells.

In one embodiment, the target cells are undifferentiated stem cells as discussed herein.

In another embodiment, the target cells are dedifferentiated stem cells as discussed herein.

In yet another embodiment, the target cells are both undifferentiated stem cells and dedifferentiated stem cells.

(A) Pharmaceutical Compositions Comprising Active Compounds

The active compounds may be administered to the cell sample in pure form or in an appropriate pharmaceutical composition.

In one embodiment, the active compounds are administered to the cell sample in a cell culture prior to transplant of the cell culture into a patient in need of cell therapy. Typically, the cell sample is a stem cell sample. Typically, the active compounds are administered to the stem cell sample prior to transplant to remove undifferentiated stem cells from the stem cell sample so that only differentiated cells are transplanted into the patient. This is important for preventing or reducing health risks such teratoma formation post-transplantation.

Following transplantation of differentiated cells into the patient who has received cell therapy, the differentiated cells may undergo dedifferentiation to form dedifferentiated stem cells. Hence, in another embodiment, the active compounds are administered to the patient after transplantation of the stem cell culture into the patient. Typically, the active compounds are administered post-transplantation to remove dedifferentiated stem cells. The active compounds may also be administered post-transplantation to remove any residual undifferentiated stem cells that have not been removed prior to transplantation.

In another embodiment, the active compounds are administered to a cell sample to remove CSCs. Cancer stem cells, like embryonic stem cells and IPSCs, have unlimited proliferative potential. Cancer stem cells can furthermore acquire the ability to metastasize. Hence, the removal of CSCs is important in cancer therapy to treat and improve survival and quality of life of cancer patients. The cell sample to which the active compounds are administered to remove CSCs may be a tissue sample (e.g. biopsy) obtained from a patient, or an organ (or part thereof) which is suspected of harboring the CSCs (e.g. lymph node, lung, breast, liver, colon, skin etc.). The cell sample may be in vivo, in vitro or ex vivo.

In general, suitable pharmaceutical compositions may be prepared according to methods which are known to those of ordinary skill in the art. The compositions comprising the active compounds disclosed herein may include a conventional pharmaceutical carrier or diluent, and in addition, may include other medicinal agents, pharmaceutical agents, carriers, adjuvants, etc. Examples of suitable pharmaceutical carriers or diluents include phosphate buffered saline solutions, water, emulsions, such as oil/water emulsions, various types of wetting agents, sterile solutions etc. Other suitable pharmaceutical carriers are described in Remington's Pharmaceutical Sciences (Mack Publishing Company), a standard reference text in this field, or in U.S. Pharmacopeia National Formulary, 1857-1853, (1990). Typically, the carrier(s) or diluent(s) will form from about 10% to about 99.9% by weight of the compositions.

Administration of the active compounds disclosed herein, in pure form or in an appropriate pharmaceutical composition, may be carried out via any of the acceptable modes of administration or pharmaceutically acceptable means of delivery. The modes of administration and pharmaceutically acceptable means of delivery may include oral administration or delivery in the form of solid, semi-solid, lyophilized powder, or liquid dosage forms. The dosage forms may include tablets, suppositories, pills, soft elastic and hard gelatin capsules, powders, solutions, suspensions, or aerosols, or the like, preferably in unit dosage forms suitable for simple administration of precise dosages.

Oral administration of the disclosed active compounds may be effected by preparing a mixture of the disclosed active compounds with an inert diluent or with an assimilable edible carrier, or they may be enclosed in hard or soft shell gelatin capsules, or they may be compressed into tablets, or they may be incorporated directly with the food of the diet. For oral therapeutic administration, the disclosed active compounds may be incorporated with excipients and used in the form of ingestible tablets, buccal tables, troches, capsules, elixirs, suspensions, syrups, wafers, and the like. Such compositions and preparations may contain the active compounds in an amount by weight percent selected from the group consisting of about 0.1% to about 70%, about 0.5% to about 65%, about 1% to about 60%, about 2% to about 55% and about 3% to about 50%.

The tablets, troches, pills, capsules and the like may also contain the following: a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin or a flavoring agent, such as peppermint, oil of wintergreen, or cherry flavoring may be added. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain sucrose as a sweetening agent, methyl and propylparabens as preservatives, a dye and flavorings, such as cherry or orange flavor. Any material used in preparing any dosage unit form should be pharmaceutically pure and substantially non-toxic in the amounts employed. In addition, the active compounds may be incorporated into sustained-release preparation and formulations.

The active compounds disclosed herein may be administered parenterally or intraperitoneally. Solutions of the disclosed active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use may include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating, such as lecithin, by the maintenance of the required particle size in the case of dispersion and by the use of surfactants. The prevention of the action of microorganisms may be brought about by various antibacterial and antifungal agents, for example, parabens, chlorobutanol, phenol, sorbic acid, thimerosal, and the like. Prolonged absorption of the injectable compositions can also be brought about by including in the composition an agent which delays absorption, for example, aluminium monostearate and gelatin.

Preferably, the pharmaceutical form may further include a suitable buffer to minimise acid hydrolysis. Suitable buffer agents are well known to those skilled in the art and include, but are not limited to, phosphates, citrates, carbonates and mixtures thereof.

The active compounds may also be administered in the form of a "prodrug". A prodrug is an inactive form of a compound which is transformed in vivo to the active form. Suitable prodrugs include esters, phosphonate esters etc, of the active form of the compound.

The active compounds in pharmaceutically acceptable form may be administered in a therapeutically effective amount which will vary depending upon a variety of factors including the activity of the specific compounds employed; the metabolic stability and length of action of the compounds; the age, body weight, general health, sex and diet of the patient; the mode and time of administration; the rate of excretion; the drug combination; the severity of the particular disease states; and the patient undergoing treatment.

Single or multiple administrations of the pharmaceutical compositions according to the invention may be carried out. One skilled in the art would be able, by routine experimentation, to determine effective, non-toxic dosage levels of the compound or composition of the invention and an administration regime which would be suitable for treating the diseases or conditions to which the compounds and compositions are applicable.

It will be apparent to one of ordinary skill in the art that the optimal course of treatment, such as the number of doses of the compound or composition of the invention given per day for a defined number of days, can be ascertained using conventional course of treatment determination tests.

Typically, an effective dosage per 24 hours for use of the active compounds in a pharmaceutical composition for removal of undifferentiated or dedifferentiated stem cells may be in the range of about 0.01 mg per kg body weight to about 250 mg per kg body weight; about 0.01 mg per kg body weight to about 200 mg per kg body weight; about 0.01 mg per kg body weight to about 150 mg per kg body weight; about 0.01 mg per kg body weight to about 100 mg per kg body weight; about 0.01 mg per kg body weight to about 50 mg per kg body weight; about 0.01 mg per kg body weight to about 25 mg per kg body weight; about 0.01 mg per kg body weight to about 10 mg per kg body weight; about 0.01 mg per kg body weight to about 5 mg per kg body weight; about 0.01 mg per kg body weight to about 1 mg per kg body weight; about 0.1 mg per kg body weight to about 250 mg per kg body weight; about 1 mg per kg body weight to about 250 mg per kg body weight; about 10 mg per kg body weight to about 250 mg per kg body weight; about 25 mg per kg body weight to about 250 mg per kg body weight; about 50 mg per kg body weight to about 250 mg per kg body weight; about 100 mg per kg body weight to about 250 mg per kg body weight; about 150 mg per kg body weight to about 250 mg per kg body weight; or about 200 mg per kg body weight to about 250 mg per kg body weight.

The active compounds of the invention may be used in combination with other known treatments or selective cytotoxic agents, for example other agents used in chemotherapy. Combinations of active agents, including the active compounds of the invention, may be synergistic.

(B) Pharmaceutical Compositions Comprising Differentiated Cells

In one embodiment, there is provided a method for preparing differentiated cells, the method comprising the steps of:
(a) removing undifferentiated stem cells or dedifferentiated stem, cells from a cell population that comprises differentiated cells, and undifferentiated stem cells or dedifferentiated stem cells, by administering to the cell population an effective amount of a compound of the formula (I), or a pharmaceutically-acceptable salt thereof, as defined herein; and
(b) culturing the remaining differentiated cells.

The undifferentiated stem cells or dedifferentiated stem cells may be selected from the group consisting of hESCs, IPSCs and CSCs.

The removal of the undifferentiated stem cells or dedifferentiated stem cells results in a cell population comprising substantially differentiated cells that can be formulated into a pharmaceutical composition. A cell population that comprises substantially differentiated cells contains at least about 60% differentiated cells, and more typically, at least about 70%, about 80%, or about 90% differentiated cells. Preferably, the cell population comprises 100% differentiated cells. For example, the cell population may comprise about 60% to about 100%, about 65% to about 100%, about 70% to about 100%, about 75% to about 100%, about 80% to about 100%, about 85% to about 100%, about 90% to about 100%, about 95% to about 100%, about 96% to about 100%, about 97% to about 100%, about 98% to about 100%, about 99% to about 100%, about 60% to about 95%, about 60% to about 90%, about 60% to about 85%, about 60% to about 80%, about 60% to about 75%, about 60% to about 70%, or about 60% to about 65% differentiated cells.

Hence, in one embodiment, there is provided a pharmaceutical composition comprising a population of differentiated cells prepared according to the method disclosed herein, and a pharmaceutically acceptable carrier. Stem cells of various types and sources may be used for preparing the pharmaceutical composition for a stem cell transplant in cell therapy. Exemplary, but non-limiting, sources include embryonic stem cells (ESCs), induced pluripotent stem cells (IPSCs), multipotent neural stem cells obtained from brain tissue, neuroblasts from newborn cerebral hemispheres, mammalian neural crest stem cells, mammalian multipotential central nervous system (CNS) stem cells, neuroepithelial stem cells, oligodendrocyte-astrocyte precursors, lineage-restricted neuronal precursors, primary liver cells such as hepatoblasts, human neonatal or fetal hematopoietic stem or progenitor cells, human mesenchymal stem cells from the bone marrow, peripheral blood or periosteum, adipose-derived stem cells, and the like. Preferably, the stem cells are ESCs and IPSCs.

The stem cells may be cultured with a medium comprising glucose, transferrin, insulin, selenium, progesterone, and several other growth factors.

The stem cells may be sourced from any vertebrate species. For example, the stem cells may be from humans; as well as non-human primates, domestic animals, livestock, and other non-human mammals.

Preferably, the stem cells are sourced from humans.

Preferably, the stem cells are human stem cells. More preferably, the stem cells are human embryonic stem cells.

Human embryonic stem cells can be prepared from human blastocyst cells using the techniques known in the art, for example as described by Thomson et al. (U.S. Pat. No. 5,843, 780; Science 282:1145, 1998; Curr. Top. Dev. Biol. 38:133 ff., 1998) and Reubinoff et al. (Nature Biotech. 18:399, 2000). Five-day old human blastocysts may be obtained from human in vivo pre-implantation embryos, from in vitro fertilized (IVF) embryos, or from one-cell human embryos that have been expanded to the blastocyst stage. Typically, the human embryos are cultured to the blastocyst stage in G1.2 and G2.2 medium, after which blastocysts that develop are selected for embryonic stem cell isolation. The zona pellucida is removed from blastocysts by brief exposure to pronase (Sigma) and the inner cell masses (ICM) isolated by immunosurgery. Typically, this is carried out by exposing the blastocysts to a 1:50 dilution of rabbit anti-human spleen cell antiserum for about 30 minutes, followed by washing of the blastocysts for 5 minutes three times in DMEM and exposure to a 1:5 dilution of Guinea pig complement (Gibco) for about 3 minutes (see Solter et al., Proc. Natl. Acad. Sci. USA 72:5099, 1975). After two further washes in DMEM, lysed trophectoderm cells may be removed from the intact ICM by gentle pipetting, and the ICM plated on murine feeder cells such as mouse embryonic fibroblasts (MEFs).

After about 9 to 15 days, ICM-derived outgrowths may be dissociated into clumps by techniques known in the art, such as but not limited to, exposure to calcium and magnesium-free phosphate-buffered saline (PBS) with 1 mM EDTA; exposure to enzymes such as dispase or trypsin; mechanical dissociation using a micropipette; and the like. The dissociated cells are re-plated on MEF, human feeder layers or extra cellular matrices (for example, Poly-D-Lysine (PDL), PDL/ fibronectin, PDL/laminin, type I collagen, Matrigel, and the like) in fresh ES medium. Colonies that form and demonstrate undifferentiated stem cell morphology are individually selected, typically using a micropipette, mechanically dissociated into clumps, and re-plated. Undifferentiated stem cell-like morphology is characterized as compact colonies with poorly discernable cell junctions but apparently high nucleus to cytoplasm ratio and prominent nucleoli. The undifferentiated stem cells are then routinely split every 1-2 weeks by brief trypsinization; exposure to Dulbecco's PBS (without calcium or magnesium and with 2 mM EDTA); exposure to type IV collagenase (about 1 mg/mL; Gibco), or by selection of individual colonies using a micropipette. Preferably, the clump sizes are of about 20 to about 100 cells.

Stem cell lines can be karyotyped using standard G-banding techniques available at commercial diagnostics laboratories, and compared to published human karyotypes. Human embryonic stem cells can also be characterized on the basis of expressed cell markers using a suitable immunological technique such as flow cytometry for membrane-bound markers (for example, GCTM-2, SSEA-3, SSEA-4, Tra-1-60, Tra-1-81, and the like), immunohistochemistry for intracellular markers (for example, Oct-4, Nanog, LIN-28, SOX2, and the like), and enzyme-linked immunoassay, for markers secreted into the medium. Alternatively, expression of protein markers can be detected at the mRNA level with reverse transcriptase-PCR using marker-specific primers (see for example, U.S. Pat. No. 5,843,780). Embryonic stem cells are also typically Oct-4 positive, and hence can be identified using antibodies such as AB3209 (Chemicon).

Other human pluripotent stem cells, such as those derived from other sources including, but not limited to embryonal carcinoma stem cells, human brain tissue, newborn cerebral hemispheres, human central nervous system, human bone marrow, human peripheral blood or periosteum, human adipose tissue, and the like, may be prepared using the above protocol.

In one embodiment, the human pluripotent stem cells are human IPSCs. Typically, human IPSCs may be prepared by isolating and culturing the donor cells, for example human fibroblasts, using techniques known in the art as described herein. The donor cells are then transfected with stem cell-associated genes using a vector, such as a viral vector (e.g. a retroviral vector, a lentiviral vector, and the like) or a plasmid. Any stem cell-associated genes may be used for the transfection. Exemplary stem cell-associated genes include OCT3, OCT4, SOX2, Klf4, c-Myc, Nanog and LIN28. The donor cells expressing the transfected genes are harvested and cultured according to ES cell culture methods using mitotically inactivated feeder cells to obtain ES-like colonies. Exemplary protocols on preparation of IPSCs are described in Yu et al. (*Science*, 2007 Dec. 21, 318(5858):1917-20) and Takahashi et al. (*Cell*, 2007 Nov. 30, 131(5):861-72, and *Nature Protocols*, 2007, 2(12):3081-89).

Differentiation of the undifferentiated stem cell culture can be initiated by first forming embryoid bodies (EB) using methods known to those skilled in the art. Typically, the cells are cultured under conditions that permit aggregates to form, for example, by allowing overgrowth of a donor stem cell culture, or by culturing the stem cells in culture vessels having a substrate with low adhesion properties which allows EB formation. Alternatively, the EB can be formed in a suspension. The EBs may be harvested by digesting with collagenase, dissociating into clusters, and plating in non-adherent cell culture plates. The aggregates are fed every few days, and then harvested after a suitable period, typically about 4 to 8 days.

Thereafter, the cells can be cultured in a medium or on a substrate that promotes enrichment of cells of a particular lineage. The substrate may comprise matrix components such as Matrigel®™ (Becton Dickenson), laminin, collagen, or gelatin. Alternatively, the matrix may be produced by culturing a matrix-producing cell line (such as a fibroblast or endothelial cell line) and then lysing and washing in a manner such that the matrix remains attached to the surface of the vessel. The embryoid bodies typically comprise a heterogeneous cell population and may have an endoderm exterior, and a mesoderm and ectoderm interior.

Alternatively, methods are known whereby the undifferentiated stem cells may be differentiated without first forming embryoid bodies by plating a suspension of undifferentiated stem cells on a solid surface that promotes differentiation. Suitable substrates include glass or plastic surfaces that are adherent, such as glass coverslips coated with a polycationic substance (e.g. polyamines like poly-lysine, poly-ornithine, etc.) The cells are then cultured in a suitable nutrient medium that is adapted to promote differentiation towards the desired cell lineage.

Differentiation may be promoted by adding a medium component that promotes differentiation towards the desired cell lineage, or inhibits the growth of cells with undesired characteristics. For example, to generate cells committed to neural or glial lineages, the medium may include brain derived neurotrophic factor (BDNF), neurotrophin-3 (NT-3), NT-4, epidermal growth factor (EGF), ciliary neurotrophic factor (CNTF), nerve growth factor (NGF), retinoic acid (RA), sonic hedgehog, FGF-8, ascorbic acid, forskolin, fetal bovine serum (FBS), and bone morphogenic proteins (BMPs) in any effective combination. To remove the undesired cells, for example undifferentiated stem cells or dedifferentiated stem cells, an active compound disclosed herein or pharmaceutical compositions thereof may be added to the culture medium during or after differentiation.

The amount of the active compound added may be in the range of about 1 µM to about 500 µM. Typically, the amount is about 1 µM to about 400 µM, about 1 µM to about 300 µM, about 1 µM to about 200 µM, about 1 µM to about 100 µM, about 1 µM to about 50 µM, about 1 µM to about 25 µM, about 2.5 µM to about 500 µM, about 5 µM to about 500 µM, about 10 µM to about 500 µM, about 20 µM to about, 500 µM, about 25 µM to about 500 µM, about 100 µM to about 500 µM, about 200 µM to about 500 µM, about 300 µM to about 500 µM, or about 400 µM to about 500 µM. Typically the active compound, or a pharmaceutical composition thereof, is added for a period of about 10 minutes, 20 minutes, 30 minutes, 40 minutes, 50 minutes, 1 h, 1.5 h, 2 h, 2.5 h, 5 h, 10 h, 12 h, 24 h, 36 h, 48 h, 60 h or 72 h. For example, the period may range from about 10 minutes to about 72 h, from about 20 minutes to about 72 h, from about 30 minutes to about 72 h, from about 40 minutes to about 72 h, from about 50 minutes to about 72 h, from about 1 h to about 72 h, from about 2 h to about 72 h, from about 5 h to about 72 h, from about 10 h to about 72 h, from about 24 h to about 72 h, from about 36 h to about 72 h, from about 48 h to about 72 h, from about 60 h to about 72 h.

Typically, the culture medium to which the active compound, or pharmaceutical composition thereof, has been added is incubated at a temperature of about 20° C., about 30° C., about 37° C. or about 40° C. For example, the incubation temperature may be about 20° C. to about 40° C., about 25° C. to about 40° C., about 30° C. to about 40° C., about 35° C. to about 40° C., about 20° C. to about 35° C., about 20° C. to about 30° C., or about 20° C. to about 25° C. Preferably, the temperature is about 37° C.

Differentiation may also be promoted by withdrawing serum or serum replacement from the culture medium using techniques known to those skilled in the art. For example, a medium devoid of serum may be substituted or replaced at the time of re-plating. Alternatively, medium components that inhibit differentiation may be removed.

Methods for obtaining tissue cell lines from stem cells are described in Pedersen (Reprod. Fertil. Dev. 6:543, 1994) and U.S. Pat. No. 6,090,622. Tissue cell lines that may be of interest in cell therapy include but are not limited to neural progenitor cells, neural restrictive cells, glial cell precursors, cardiac muscle and cardiomyocytes, hematopoietic progenitors, glucose-responsive insulin secreting pancreatic beta cells, hepatocyte precursor cells, chondrocytes, osteoblasts, retinal pigment epithelial cells, fibroblasts, skin cells such as keratinocytes, dendritic cells, hair follicle cells, renal duct epithelial cells, smooth and skeletal muscle cells, testicular progenitors, and vascular endothelial cells.

The differentiated cells prepared as discussed herein are relatively homogenous cell populations that have been depleted of undifferentiated or dedifferentiated stem cells. The homogenous cell populations, may be formulated into a suitable pharmaceutical formulation for use in medicine and research.

In medicine, the differentiated cells prepared by the methods disclosed herein may be used for tissue reconstitution or regeneration in a human patient in need thereof. The cells may be administered in a manner that permits them to graft to the intended tissue site and reconstitute or regenerate the functionally deficient area. The composition may be administered via intravenous injection. Preferably, the cells are in solution, e.g. buffered saline. For example, neural stem cells may be transplanted directly into parenchymal or intrathecal sites of the CNS, typically using single cell suspension or small aggregates having a density of about 25,000 to about 500,000 cells per mL, about 25,000 to about 450,000 cells per mL, about 25,000 to about 400,000 cells per mL, about 25,000 to about 350,000 cells per mL, about 25,000 to about 300,000 cells per mL, about 25,000 to about 250,000 cells per mL, about 25,000 to about 200,000 cells per mL, about 25,000 to about 150,000 cells per mL, about 25,000 to about 100,000 cells per mL, about 25,000 to about 75,000 cells per mL, about 25,000 to about 50,000 cells per mL, about 50,000 to about 500,000 cells per mL, about 75,000 to about 500,000 cells per mL, about 100,000 to about 500,000 cells per mL, about 150,000 to about 500,000 cells per mL, about 200,000 to about 500,000 cells per mL, about 250,000 to about 500,000 cells per mL, about 300,000 to about 500,000 cells per mL, about 350,000 to about 500,000 cells per mL, about 400,000 to about 500,000 cells per mL, or about 450,000 to about 500,000 cells per mL. The neural stem cells are useful in treatment of both acute and chronic diseases of the nervous system, for example epilepsy, stroke, ischemia, Huntington's disease, Parkinson's disease and Alzheimer's disease. Stem cell preparations enriched in oligodendrocytes or oligodendrocyte precursors are useful in treating dysmyelinating disorders such as Pelizaeus-Merzbacher disease, multiple sclerosis, leukodystrophies, neuritis and neuropathies, while stem cell preparations enriched in hepatocytes and hepatocyte precursors are useful for repairing liver damage caused by hepatic failure. Similarly, stem cell preparations enriched in cardiomyocytes are useful for treating damage caused by cardiac injury, regenerating cardiac muscle and treating insufficient cardiac function.

The number of cells in the composition will be an amount effective to treat the particular condition that is in need of cell therapy. The cells may express a marker, e.g., green fluorescent protein (GFP), to facilitate detection of the site at which the cells have become stably engrafted in the patient. In some instances where the cells do not become stably engrafted at the target site, or when used to treat chronic diseases (e.g. autoimmune disorders), multiple dosages of the composition may be administered.

Alternatively, the cells are in a semi-solid or solid support, such as a fibrin-based biomatrix. The biomatrix can be prepared in vitro and then transplanted into a patient to deliver the cells to the target site in vivo that is in need of the cell therapy.

In research, the differentiated cells prepared by the methods disclosed herein may be used in screening for factors (e.g. small molecule drugs, peptides, polynucleotides, and the like) and environmental conditions (e.g. culture conditions) that affect the characteristics of differentiated cells. For example, the differentiated cell preparations may be used to screen factors that promote maturation, proliferation and maintenance of such cells in long-term culture. This can be achieved by mixing a candidate factor to the cell preparation and then determining any phenotypic changes that may result. The differentiated cell preparations may also be used to screen compounds in drug research using methods known in the art (see for e.g. "In vitro Methods in Pharmaceutical Research", Academic Press, 1997). For example, the differentiated cell preparations may be combined with a candidate drug compound and then determining any change in the morphology, marker phenotype, or metabolic activity of the cells that is attributable to the compound (compared with untreated cells or cells treated with an inert compound), and correlating the effect of the compound with the observed change. Two or more drugs may also be tested in combination either simultaneously or sequentially, to detect possible drug-drug interaction effects.

BRIEF DESCRIPTION OF DRAWINGS

The accompanying drawings illustrate a disclosed embodiment and serve to explain the principles of the disclosed embodiment. It is to be understood, however, that the drawings are designed for purposes of illustration only, and not as a definition of the limits of the invention.

show untreated hESC while the images on the right (C and D) show hESC treated with 40 μM of JC010 for 24 hours. The arrows indicate trypan blue positive dead cells.

Figure 6:
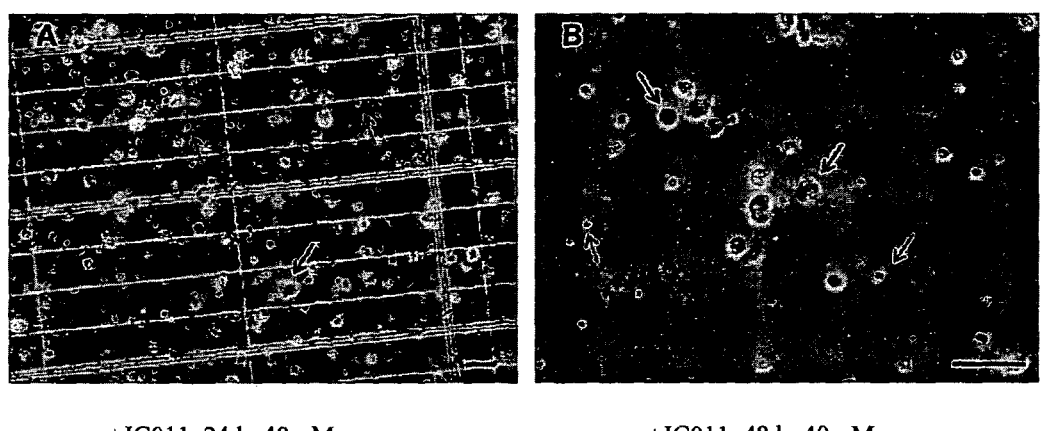

FIG. 6 shows light microscopic images of hESC killing after treatment with JC011 in a trypan blue cell viability assay. The image on the left (A) shows hESC treated with 40 μM of JC011 after 24 hr at a magnification of 200× while the image on the right (B) shows hESC treated with 40 μM of JC011 after 48 hr at a magnification of 400×.

Figure 7A:
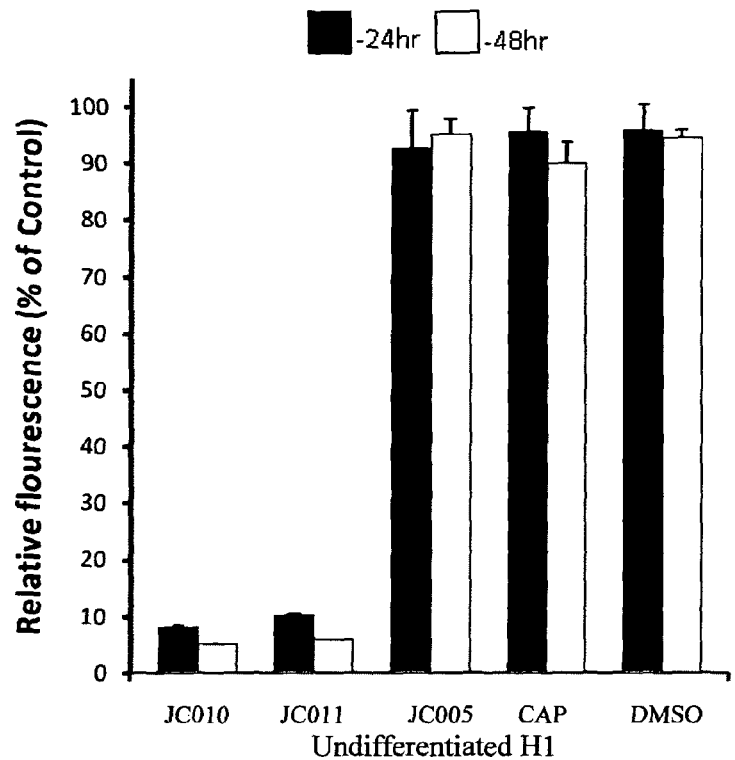
Figure 7B:
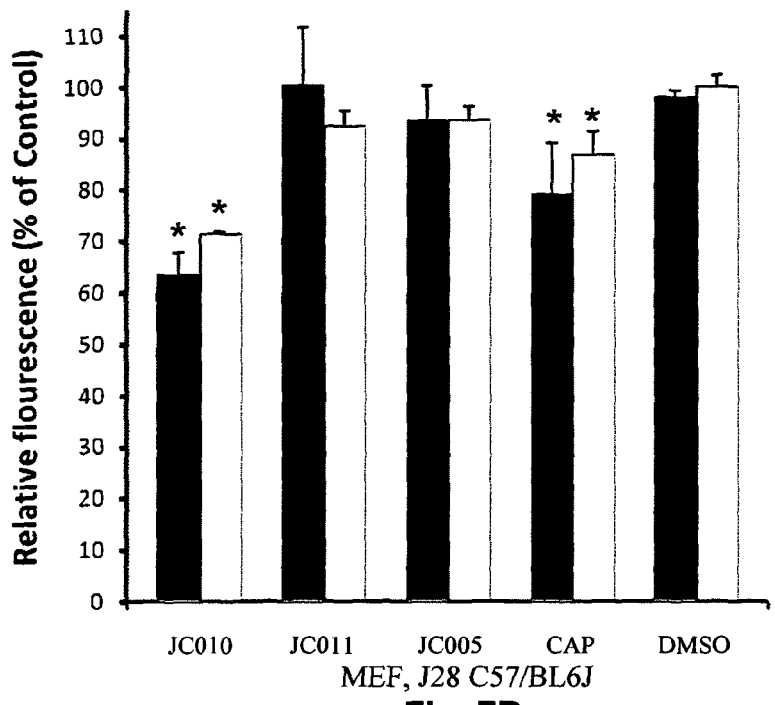

FIG. 7 shows the results of a resazurin cell viability assay on hESC (A) and murine feeder cells (mouse embryonic fibroblasts (MEFs)) (B) treated with capsaicin analogues JC010, JC011 and JC005, capsaicin (CAP), and DMSO after 24 hr and 48 hr. The hESCs used are undifferentiated H1 cells, while the murine feeder cells (mouse embryonic fibroblasts (MEFs)) used are J28 C57/BL6J cells. The columns represent the means of 4 experiments while the bars represent relative fluorescence ±s.d. The control was untreated hESCs and untreated murine feeder cells (mouse embryonic fibroblasts (MEFs)) with a final DMSO concentration of 1% v/v while the final sample concentration was 40 μM. * denotes P<0.01, Student's T-test, 2-tail.

FIG. 8 shows the effects of the analogues JC005, JC010, JC011, JC017, JC025 and JC026 on the hESC cell line BGO1v (A) and on normal human primary astrocytes (B). The columns represent the means of 4 experiments while the bars represent relative fluorescence ±s.d. The final DMSO concentration was 1% v/v and the final sample concentration was 40 μM.

Figure 9:
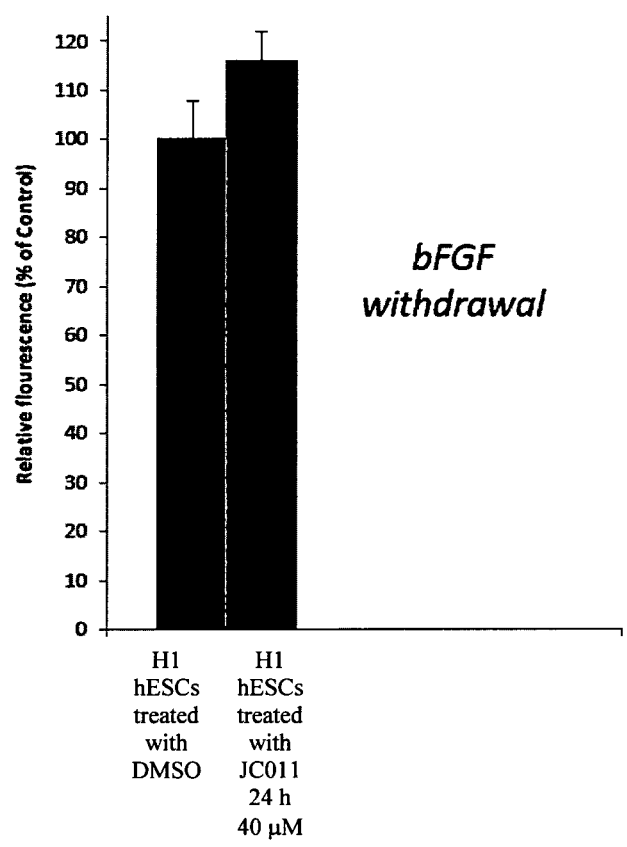

FIG. 9 shows the results of a resazurin cell viability assay on differentiated hESCs (H1) treated with 1% v/v DMSO, or 40 μM of JC011 after 24 hr.

Figure 10:
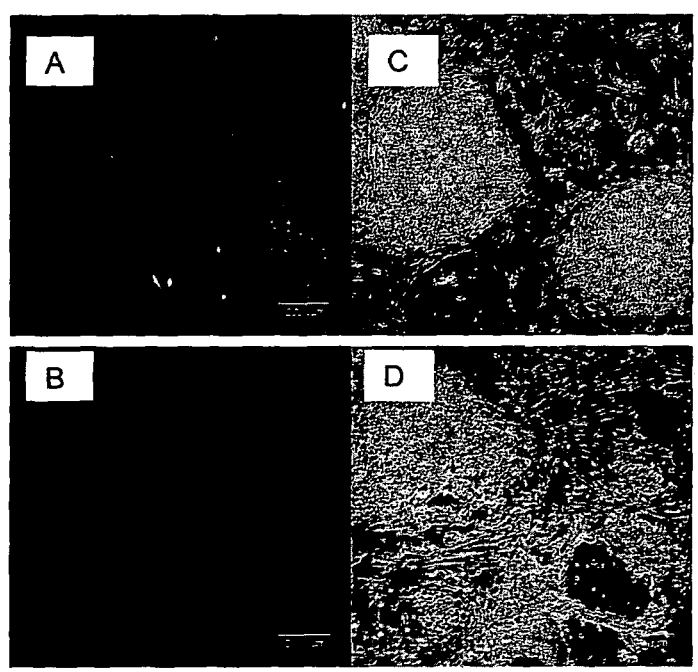

FIG. 10 shows fluorescence (left panel) and light (right panel) microscopic images of dichlorofluorescin diacetate (DCFH-DA) analysis on untreated Wicell H1 cells (images A and C) and Wicell H1 cells treated with 12.5 μg/mL of JC011 after 3 hr (images B and D).

FIG. 11 shows the dose response curves for capsaicin analogues JC010 and JC011 on undifferentiated hESCs (A) and differentiated hESCs (B).

Figure 12:
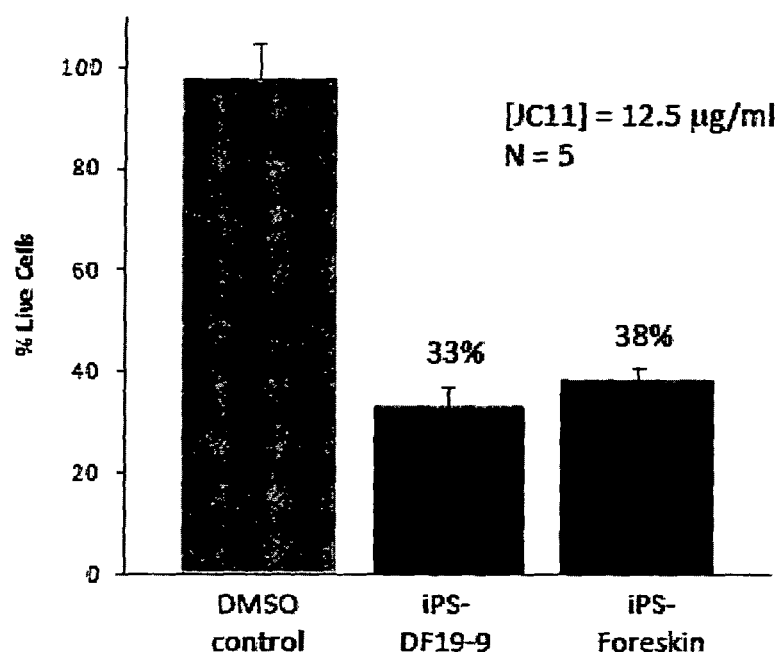

FIG. 12 shows the cytotoxic effect of analogue JC011 on IPS-DF19-9 cells and foreskin-derived IPSCs (IPS-Foreskin).

Figure 13:
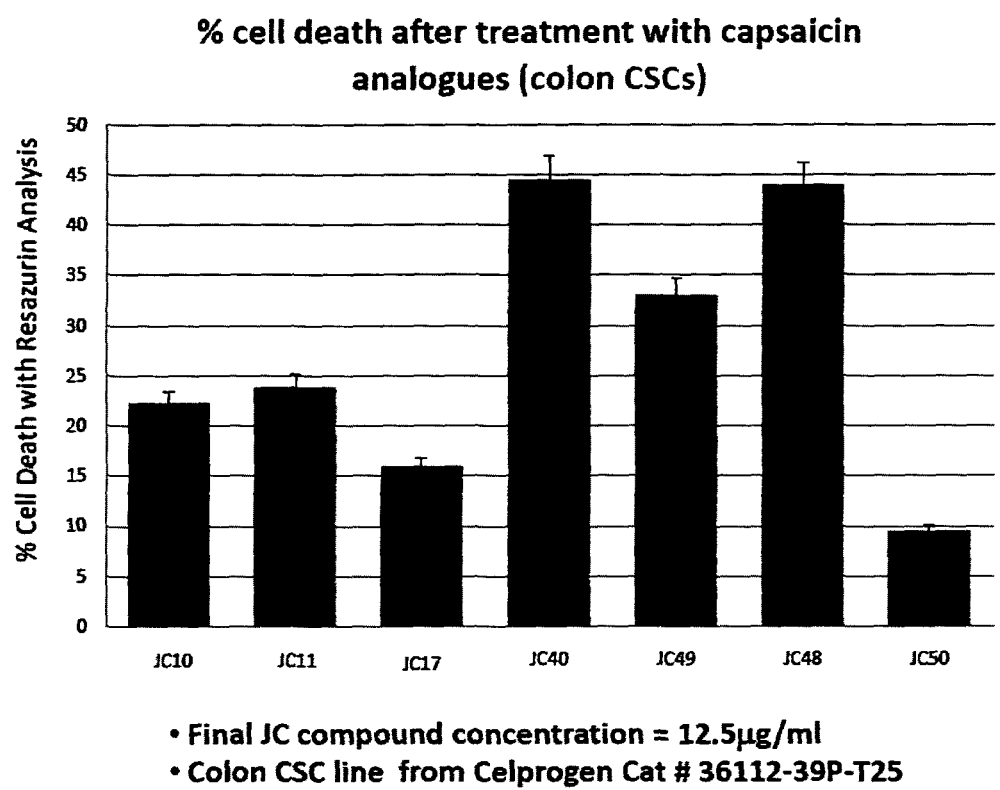

FIG. 13 shows the cytotoxic effect of analogues JC010, JC011, JC017, JC040, JC049, JC048 and JC050 in concentrations of 12.5 μg/mL on CSCs derived from a colon CSC line.

Figure 14:
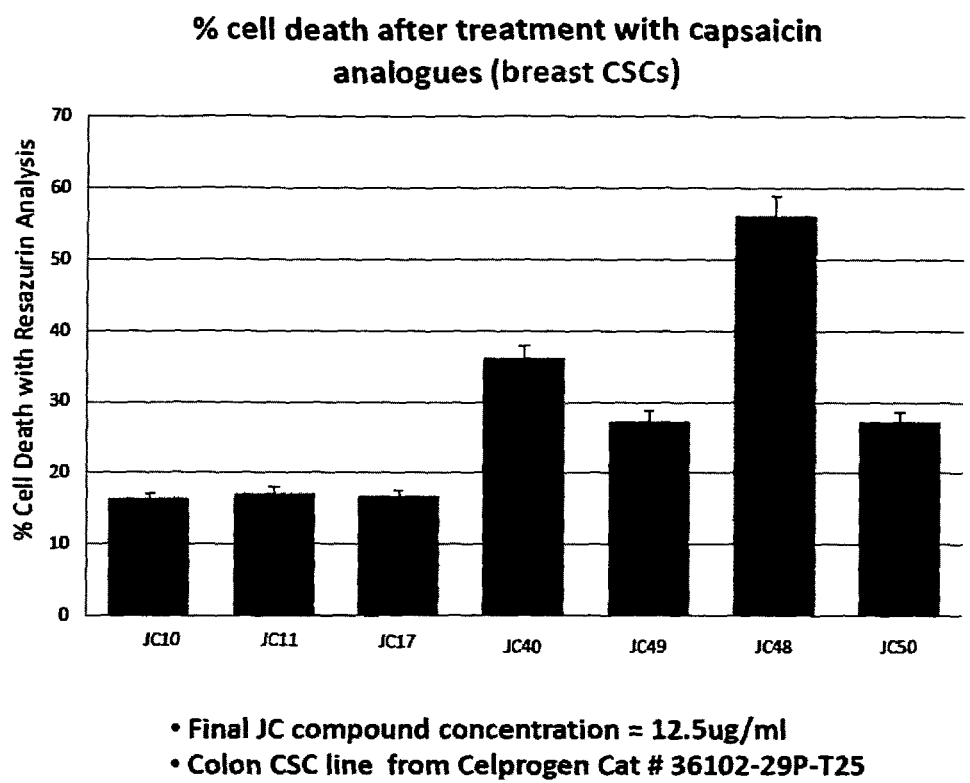

FIG. 14 shows the cytotoxic effect of analogues JC010, JC011, JC017, JC040, JC049, JC048 and JC050 in concentrations of 12.5 μg/mL on CSCs derived from a breast CSC line.

BEST MODE

Non-limiting examples of the invention, including the best mode, and comparative examples will be further described in greater detail by reference to specific examples, which should not be construed as in any way limiting the scope of the invention.

Synthesis of Capsaicin Analogues

Materials

The chemical reagents and solvents used in the following examples were purchased from Sigma-Aldrich and Merck.

Analytical Protocols (a) Analytical High Performance Liquid Chromatography (HPLC)

Analytical HPLC was performed on a Waters HPLC system equipped with a Waters 2998 PDA detector, Waters 2695 separation module using a Phenomenex Luna C18(2) (4.6 mm I.D.×150 mm, 5μ) column. A gradient elution starting with 20% CH$_3$CN, 80% (0.1% formic acid/H$_2$O), and ending with 100% CH$_3$CN at a flow rate of 1.0 mL/min over 15 min was used.

(b) Preparative HPLC

Preparative HPLC was performed on a Shimadzu LC-8A HPLC system equipped with: a CBM-20A PDA detector, Gilson 215 liquid handler and fraction collector using a X-Bridge Prep C$_{18}$ (30 mm I.D.×50 mm, 5μ) column. An isocratic elution with 20% CH$_3$CN, 80% (0.1% formic acid/H$_2$O) at a flow rate of 20.0 mL/min for 5 min was used. This was followed by a gradient elution starting with 20% CH$_3$CN, 80% (0.1% formic acid/H$_2$O), and ending with 100% CH$_3$CN at a flow rate of 20.0 mL/min over 45 min.

(c) Liquid Chromatography-mass Spectrometry (LC-MS)

LC-MS data was collected on a Shimadzu LCMS-IT-TOF instrument equipped with SPD-M20A PDA detector, LCMS-IT-TOF MS detector and LC-20AD binary gradient pump using a Shimpack VP-ODS (2.0 mm I.D.×150 mm) column. An isocratic elution with 20% H$_2$O and 80% CH$_3$CN at a flow rate of 0.2 mL/min over 3 min was used.

EXAMPLE 1

Synthetic Procedure for Analogues JC011, JC040, JC048, JC049 and JC050

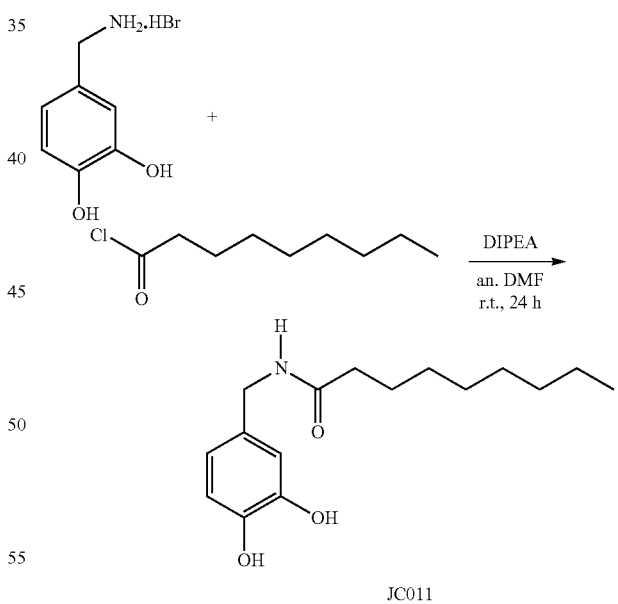

JC011

To a solution of 3,4-dihydroxybenzylamine hydrobromide (1 mmol) in anhydrous N,N-dimethylformamide (DMF) (2 mL) was added N,N-diisopropylethylamine (DIPEA) (2 mmol) to liberate the amine. After stirring at room temperature for 10 min, nonanoyl chloride (1 mmol) was added. The solution was stirred at room temperature for 24 h. After the reaction, water (40 mL) was added to the solution. The reaction mixture was transferred to a separating funnel and extracted with dichloromethane, CH$_2$Cl$_2$ (3×6 mL). The organic extracts were concentrated under reduced pressure to give a crude JC011 product. The crude JC011 product was then purified by silica gel column chromatography (using hexane/ethyl acetate, 2:1 v/v, as eluent) or preparative HPLC (using the protocol set out in "Analytical Protocols" above) to give the final JC011 product.

Analogues JC040, JC048, JC049 and JC050 were prepared using the same procedure as JC011 except that the nonanoyl chloride was replaced with decanoyl chloride for JC040, dodecanoyl chloride for JC048, undecanoyl chloride for JC049, and tetradecanoyl chloride for JC050.

EXAMPLE 2

Synthetic Procedure for Analogues JC010 and JC017

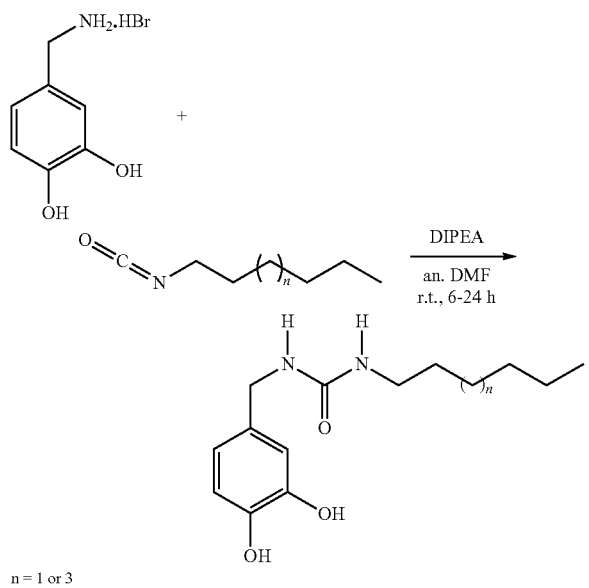

n = 1 or 3

To a solution of 3,4-dihydroxybenzylamine hydrobromide (1-2 mmol) in anhydrous dimethylformamide (DMF) (2-4 mL) was added N,N-diisopropylethylamine (DIPEA) (1-2 mmol) to liberate the amine. After stirring at room temperature for 10 min, isocyanate (1-2 mmol) was added. The solution was stirred at room temperature for 6 to 24 h. After the reaction, water (20 mL) was added to the solution. The reaction mixture was transferred to a separating funnel and extracted with dichloromethane, $CH_2Cl_2$ (3×10 mL). The organic extracts were concentrated under reduced pressure to give a crude product, which was purified by silica gel column chromatography (using hexane/ethyl acetate, 2:1 v/v, as eluent) or preparative HPLC (using the protocol set out in "Analytical Protocols" above) to give the final product.

For analogues that precipitated during the extraction process with dichloromethane, the suspension containing the precipitated analogues was transferred to a Falcon tube and centrifuged. The supernatant was discarded. The pellet was re-suspended with ethyl acetate (5 mL) and centrifuged. The re-suspension and centrifugation steps were carried out twice. The crude product obtained was further purified by preparative HPLC (using the protocol set out in "Analytical Protocols" above).

EXAMPLE 3

Synthetic Procedure for Analogue JC005

The same protocol as set out in Example 1 for the analogue JC011 was used to prepare JC005, except that the following hydrochloride salt of an amine was used:

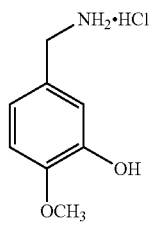

EXAMPLE 4

Synthetic Procedure for Analogues JC025 and JC026

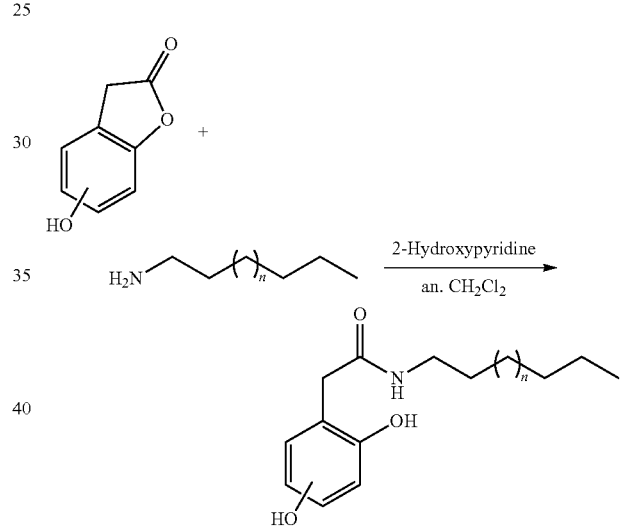

n = 1 or 3

To a solution of lactone (2 mmol) and 2-hydroxypyridine (0.2 mmol) in anhydrous dichloromethane (5 mL) was added an amine (2.2 mmol). The mixture was stirred at room temperature for 6 to 24 h. After the reaction, water (20 mL) was added. The reaction mixture was transferred to a separating funnel and extracted with dichloromethane, $CH_2Cl_2$ (3×10 mL). The solvent extracts were concentrated under reduced pressure to give a crude product, which was purified by silica gel column chromatography (using hexane/ethyl acetate, 1:1 v/v as eluent) or preparative HPLC (using the protocol set out in "Analytical Protocols" above) to give the final product.

EXAMPLE 5

Analytical Data on Capsaicin Analogues

The capsaicin analogues prepared in Examples 1-4 above were analyzed using the analytical protocols set out above. The resulting mass spectral, yield and purity data for each analogue are tabulated in Table 1 below.

TABLE 1

| Test Sample | Structure | Exact Mass (calculated) | Exact Mass (observed) | Purified Yield (%) | HPLC Purity (%) |
|---|---|---|---|---|---|
| JC005 | (4-methoxy-3-hydroxybenzyl)octanamide | 294.2069 [M + H]$^+$ | 294.2055 [M + H]$^+$ | 81.5 | 98 |
| JC010 | 1-(3,4-dihydroxybenzyl)-3-octylurea | 295.2022 [M + H]$^+$ | 295.2011 [M + H]$^+$ | 9.8 | >99 |
| JC011 | (3,4-dihydroxybenzyl)octanamide | 280.1913 [M + H]$^+$ | 280.1905 [M + H]$^+$ | 30.3 | >99 |
| JC017 | 1-(3,4-dihydroxybenzyl)-3-hexylurea | 267.1709 [M + H]$^+$ | 267.1704 [M + H]$^+$ | 2.6 | >99 |
| JC025 | 2-(2,5-dihydroxyphenyl)-N-hexylacetamide | 252.1600 [M + H]$^+$ | 252.1594 [M + H]$^+$ | 49.4 | >99 |
| JC026 | 2-(2,5-dihydroxyphenyl)-N-octylacetamide | 280.1913 [M + H]$^+$ | 280.1901 [M + H]$^+$ | 22.0 | 71 |

TABLE 1-continued

Analytical Data on Capsaicin Analogues

| Test Sample | Structure | Exact Mass (calculated) | Exact Mass (observed) | Purified Yield (%) | HPLC Purity (%) |
|---|---|---|---|---|---|
| JC040 | (vanillylamide of C10 acyl chain) | 294.2064 [M + H]⁺ | 294.2059 [M + H]⁺ | 52 | 99 |
| JC048 | (vanillylamide of C12 acyl chain) | — | — | 50 | >99 |
| JC049 | (vanillylamide of C11 acyl chain) | — | — | 95 | >99 |
| JC050 | (vanillylamide of C13 acyl chain) | — | — | 87 | >99 |

Effect of Capsaicin Analogues JC010, JC011, JC017, JC040, JC048, JC049 and JC050 on Human Embryonic Stem Cells, IPSCs and CSCs Resazurin Cell Viability Assay The resazurin cell viability assay was conducted on hESC, differentiated hESCs, osteoblasts, murine feeder cells (mouse embryonic fibroblasts (MEFs)), IPSCs derived from foreskin (IPS-DF19-9 and IPS-foreskin) and CSCs (colon CSCs and breast CSCs). The assay is based on the use of an indicator dye resazurin to measure the metabolic capacity of a cell. A viable cell would retain the ability to reduce resazurin to resorufin, which is a highly fluorescent compound. Conversely, a non-viable cell would rapidly lose its metabolic capacity, and hence would not reduce the resazurin to generate the fluorescent resorufin signal.

The template of a 96-well plate in a resazurin cell viability assay is as follows:

|   | 1 | 2 | 3 | 4 | 5 | 6 | 7 | 8 | 9 | 10 | 11 | 12 |
|---|---|---|---|---|---|---|---|---|---|---|---|---|
| A | S | S | S | S | S | S | S | S | S | S | Negative Control | Blank |
| B | S | S | S | S | S | S | S | S | S | S | Negative Control | Blank |
| C | S | S | S | S | S | S | S | S | S | S | Negative Control | Blank |
| D | S | S | S | S | S | S | S | S | S | S | Negative Control | Blank |
| E | S | S | S | S | S | S | S | S | S | S | Negative Control | Blank |
| F | S | S | S | S | S | S | S | S | S | S | Negative Control | Blank |
| G | S | S | S | S | S | S | S | S | S | S | Negative Control | Blank |
| H | S | S | S | S | S | S | S | S | S | S | Negative Control | Blank |

In wells A1-H10, 10 µl/well test sample in DMSO and 190 µl/well 150 µM resazurin were added.

In wells A11-H11, 10 μl/well DMSO and 190 μl/well 150 μM resazurin were added as negative controls.

In wells A12-H12, 200 μl/well DMSO were added to provide the Blank reading.

Data Processing:

The percentage of the resazurin activity was calculated based on the following equation:

$$\% \text{ activity} = \left(\frac{(Sample_{OD517\ nm} - Blank_{OD517\ nm})}{(Negative\ Control_{OD517\ nm} - Blank_{OD517\ nm})}\right) \times 100 \quad \text{(Eq. 1)}$$

The percentage of cell death was calculated based on the following equation:

$$\% \text{ cell death} = 100 - \% \text{ activity} \quad \text{(Eq. 2)}$$

The cells were plated in a 96-well multi-well plate 5 days before the assay. 200 μL of medium containing $10^5$/mL cells (i.e. $2 \times 10^4$ cells) were used for each well.

The cells were then treated with 12.5 μg/mL of the capsaicin analogues. The final concentration of DMSO used as control was 1% v/v.

The cells were then incubated at 37° C. for about 16 h overnight in 5% $CO_2$. The media was then removed from the wells and 100 μL of PBS buffer was added to each well. 20 μL of resazurin was added to each well to give a final resazurin concentration of 8 μg/mL. The plates were further incubated at 37° C. for 2 h, after which the plate was read at an excitation wavelength of 535 nm and an emission wavelength of 590 nm with a Tecan Infinite 200 microplate reader.

Trypan Blue Cell Viability Assay

The Trypan Blue cell viability assay was conducted by first diluting 10 μL of a cell suspension with 10 μL of 0.4% w/v Trypan Blue solution. The cell suspension and Trypan Blue solution were mixed using a pipette, after which the mixture was incubated at room temperature for 10 minutes. 20 μL of the mixture was then loaded into a charged hemocytometer for visualization under 10× and 20× magnification phase optics microscopy. Cells which stain blue are dead cells.

Dichlorofluorescein Diacetate (DCFH-DA) Analysis

Live adherent cells were washed with PBS solution. DCHF-DA solution was then added to the cells in PBS solution at a final working concentration of 10 μM. The mixture was then incubated at room temperature for 5 minutes, and visualized under a fluorescence microscope with FITC filters. Bright green fluorescent cells are indicative of cells with a high content of reactive oxygen species (ROS).

EXAMPLE 6 hESC-Selective Killing Induced by JC010, JC011 and JC017

Using the above cell viability assays, various cell types including hESCs, differentiated hESCs, human primary astrocytes and murine feeder cells (mouse embryonic fibroblasts (MEFs)) were treated with one of the analogues synthesized in Examples 1 to 3. The cells were then visualized with 5×, 10×, 20× and 40× objectives using dark field, phase optics and fluorescence microscopy with an Olympus IX51 inverted microscope or Leica MZ8 stereomicroscope.

Figure 1:
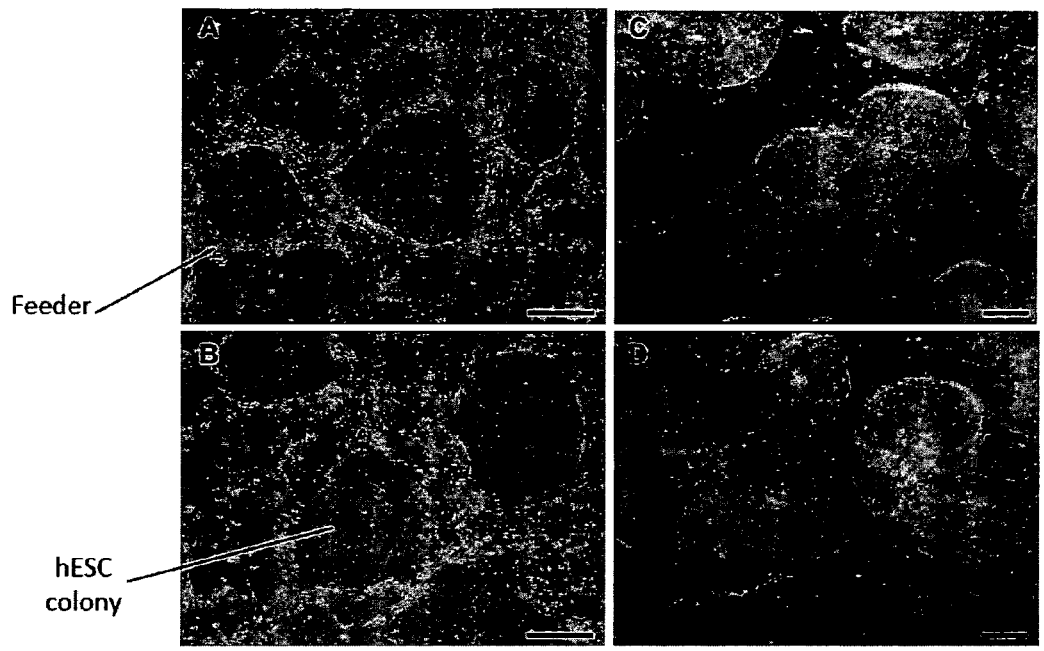
FIG. 1 shows light microscopic images of normal untreated and undifferentiated human embryonic stem cell (hESC) colonies and murine feeder cells (mouse embryonic fibroblasts (MEFs)) at a magnification of 50×. Images (A) and (B) are phase contrast optic images, while images (C) and (D) are dark field images.

FIG. 1 shows light microscopic images of normal untreated and undifferentiated human embryonic stem cell (hESC) colonies and murine feeder cells (mouse embryonic fibroblasts (MEFs)). In the phase contrast optics images (FIGS. 1A and 1B), the hESCs are seen as dark colonies surrounded by the murine feeder cells (mouse embryonic fibroblasts (MEFs)). In the dark field images (FIGS. 1C and 1D), the hESCs are seen as bright colonies surrounded by the murine feeder cells (mouse embryonic fibroblasts (MEFs)).

Figure 2:
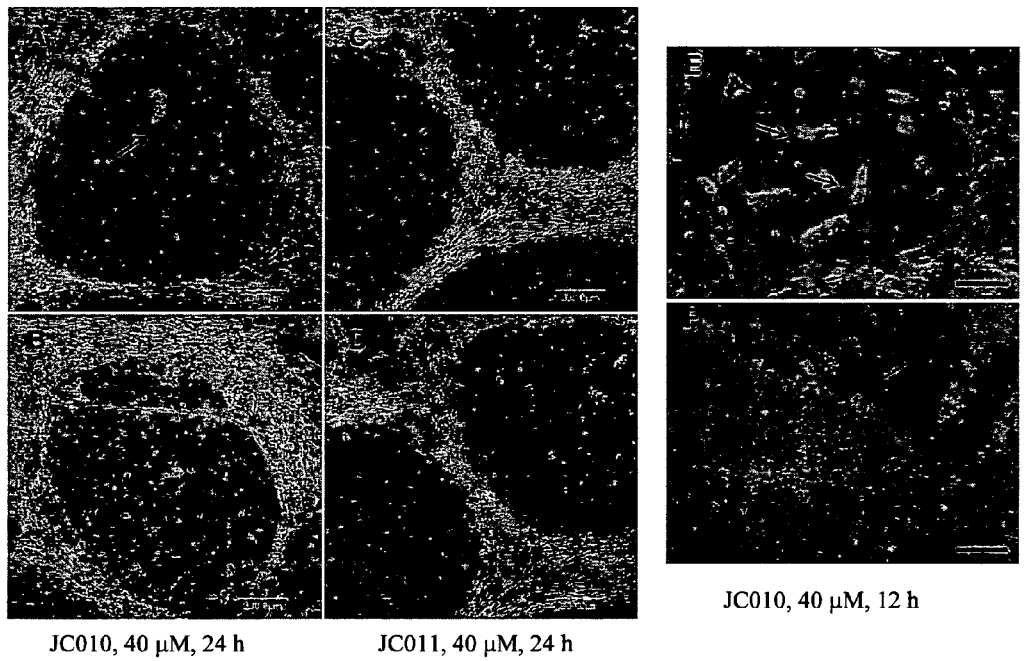
FIG. 2 shows light microscopic images of hESC-selective killing induced by 40 μM of JC010 for 12 hours (images E and F) and 24 hours (images A and B), and by 40 μM of JC011 for 24 hours (images C and D) at a magnification of 100×.

The light microscopic images in FIG. 2 show the selective and rapid killing of hESCs induced by 40 μM of JC010 for 12 and 24 hours, and by 40 μM of JC011 for 24 hours. The dead hESC debris is identified by the arrows in. FIGS. 2A, 2E and 2F. A "hollowing-out" effect can clearly be seen in these images, where the colonies of hESCs are selectively killed to leave a hollow space surrounded by feeder cells.

Figure 3:
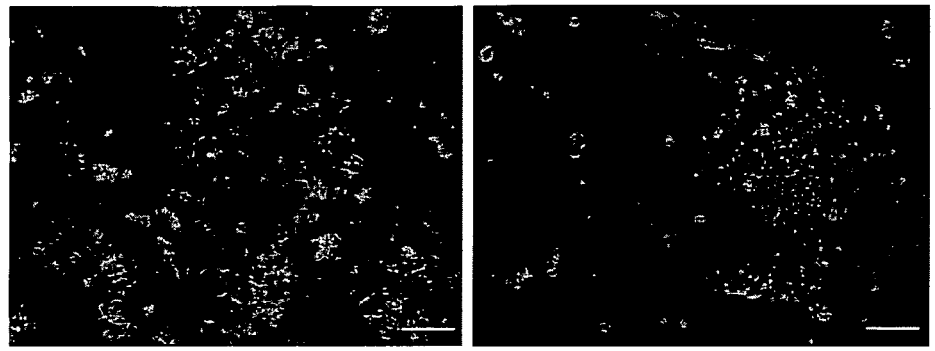
FIG. 3 shows light microscopic images of hESC-selective killing induced by 40 μM of JC017 for 12 hours at a magnification of 100×.

The light microscopic images in FIG. 3 show the effect of analogue JC017 on hESCs after 12 hours. When compared to FIG. 2, it can be seen that the killing effect of analogue JC017 on hESCs was not as selective nor as potent as the effect of the analogues JC010 and JC011. This is because, the murine feeder cells (mouse embryonic fibroblasts (MEFs)), not only the hESCs, were also affected, and there was no "hollowing-out" effect.

Figure 4:
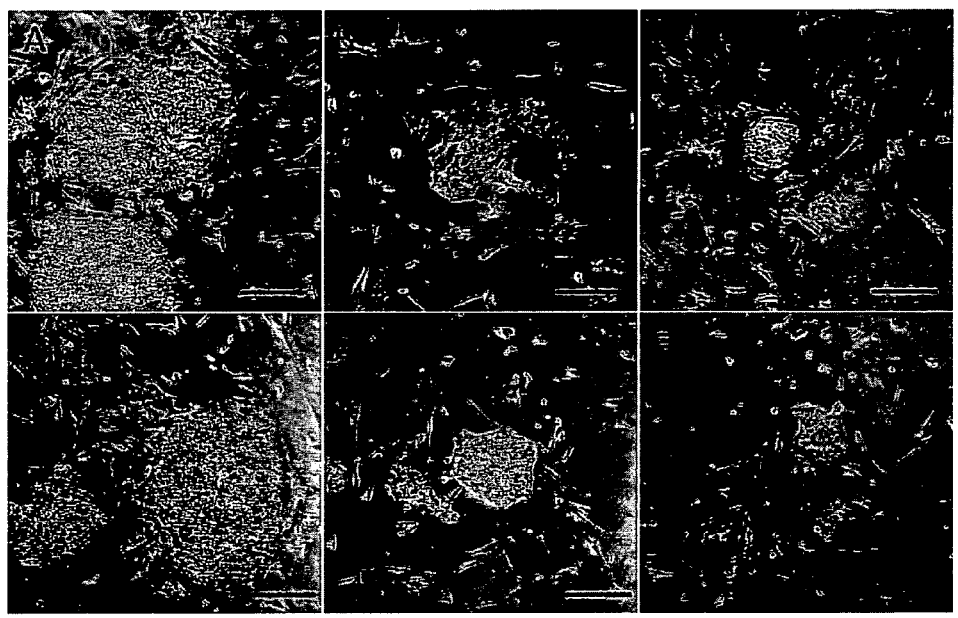
FIG. 4 shows light microscopic images of the effect of capsaicin analogues JC010 and JC011 on the growth of hESCs and murine feeder cells (mouse embryonic fibroblasts (MEFs)) after 24 hr incubation at a magnification of 100×. Image (A) shows the DMSO control; image (B) shows the sample in which 2.5 μg/mL (8 μM) JC010 was used; image (C) shows the sample in which 12.5 μg/mL (40 μM) JC010 was used; image (D) shows the sample in which 12.5 μg/mL (40 μM) JC005 was used; image (E) shows the sample in which 2.5 μg/mL (8 μM) JC011 was used; and image (F) shows the sample in which 12.5 μg/mL (40 μm) JC011 was used.

In FIG. 4, the light microscopic images show that the analogues JC010 and JC011 were effective at selective killing of hESCs at low concentrations (2.5 μg/mL and 12.5 μg/mL). In FIG. 4(A), no killing of cells was seen when the cells were cultured with only DMSO. In FIGS. 4(B), (C), (E) and (F), it can be seen that the hESCs were selectively killed when the cells were cultured with 2.5 μg/mL of JC010, 12.5 μg/mL of JC010, 2.5 μg/mL of JC011, and 12.5 μg/mL of JC011, respectively. No such killing effect was seen with another analogue J0005 in FIG. 4(D).

Figure 5:
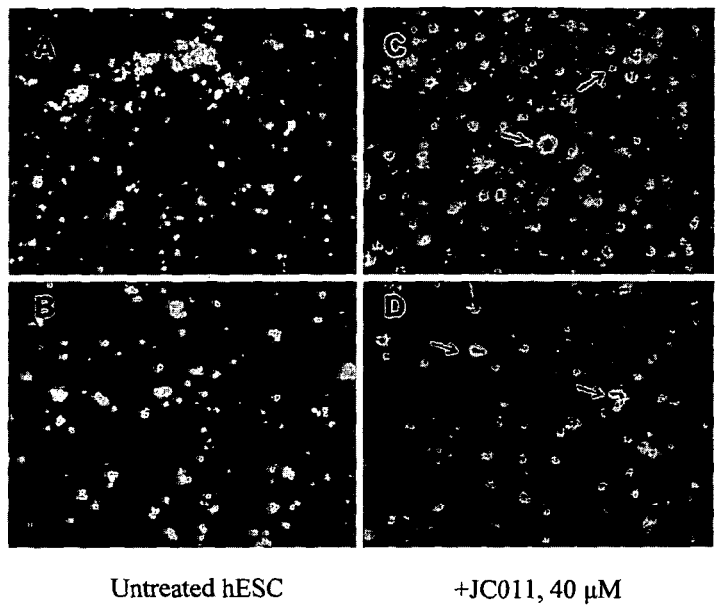
FIG. 5 shows light microscopic images of hESC killing after treatment with JC010 in a trypan blue cell viability assay at a magnification of 200×. The images on the left (A and B)

The results of the treatment of hESCs with JC010 and JC011 in an alternative cell viability assay, the Trypan Blue assay, are shown in FIGS. 5 and 6, respectively. It can be seen in the treated samples, that wide spread killing of hESC occurred even at the relatively low concentration of 40 μM of JC010 (FIG. 5) and JC011 (FIG. 6), as compared to the untreated hESC. It can be seen that, in the treated samples, there is a lot of cell debris (stained blue and shown by arrows in FIGS. 5 and 6) and very few intact cells.

In FIG. 7, it can be seen that the relative fluorescence of the JC010 and JC011 treated undifferentiated hESCs (H1 cells) were significantly lower than those treated with JC005, capsaicin (CAP) and DMSO(P<0.0001, Student's T-test, 2 tail). In comparison, the relative fluorescence of the JC010 and JC011 treated murine feeder cells (mouse embryonic fibroblasts (MEFs)) were not significantly different from those treated with JC005, capsaicin (CAP) and DMSO (P<0.01, Student's T-test, 2 tail). Hence, it can be seen from FIG. 7 that JC010 and JC011 were selective for the H1 hESCs, and this effect was potent and could be seen after only 24 h of incubation.

Figure 8A:
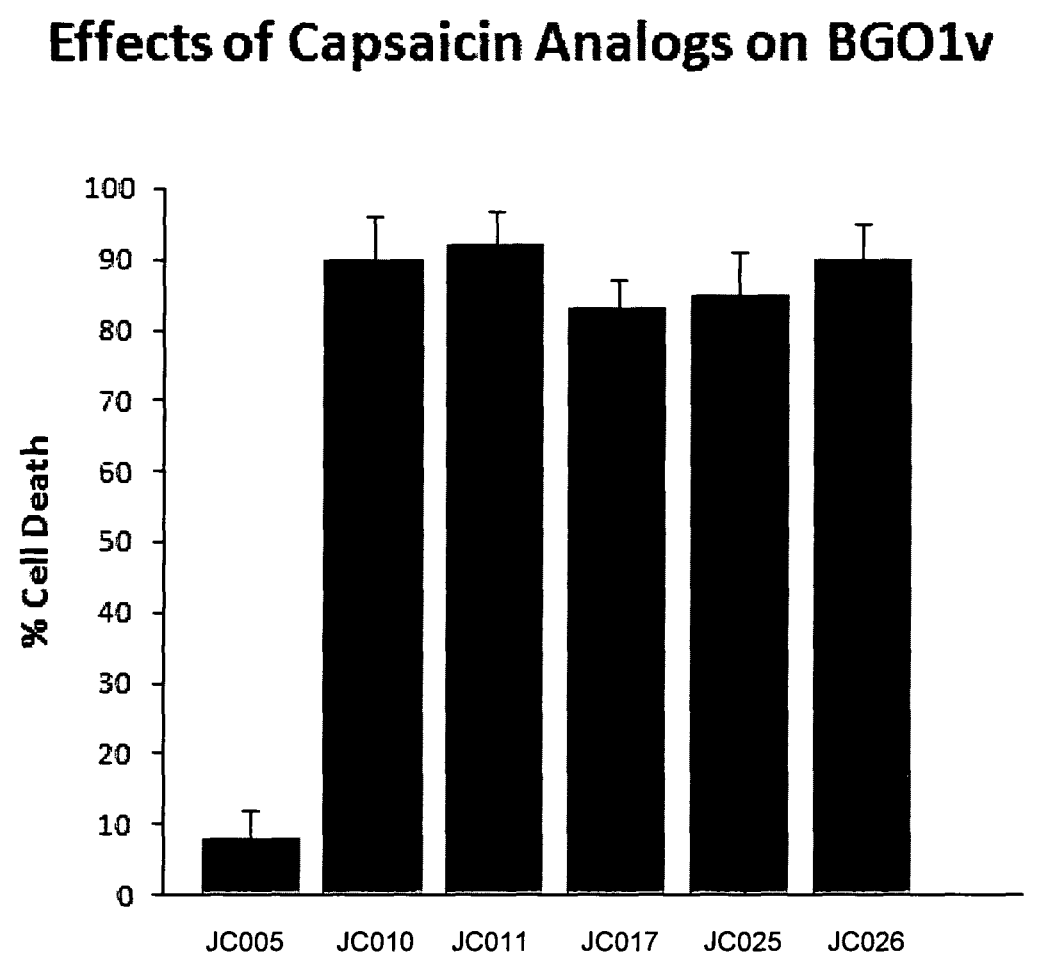
Figure 8B:
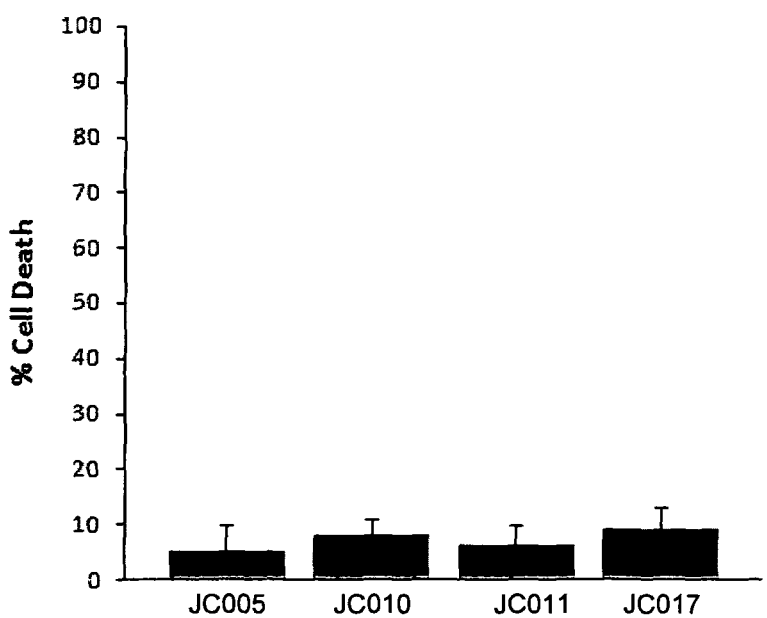

FIG. 8A shows the effects of the analogues JC005, JC010, JC011, JC017, JC025 and JC026 on the hESC cell line BGO1v. FIG. 8B shows the effects of the analogues JC005, JC010, JC011 and JC017 on normal human primary astrocytes. The analogues JC010, JC011 and JC017 selectively killed the hESCs (as reflected by the high percentages of cell death) but not the normal human primary astrocytes (as reflected by the low percentages of cell death). These results are consistent with those in FIG. 7 above in that the analogues JC010 and JC011 are selective for hESCs and not the normal differentiated cells. JC005 on the other hand, is not cytotoxic to either hESCs or normal human primary astrocytes as reflected by the low, percentages of cell deaths of both cell types caused by JC005.

bGFG is a critical growth factor that maintains the hESCs in the undifferentiated state. Removal or withdrawal of bGFG induces hESCs to undergo differentiation. FIG. 9 shows the data for differentiated cells where bGFG has been withdrawn. In FIG. 9, it can be seen that JC011 did not kill differentiated hESCs as the relative fluorescence of the sample incubated with JC011 was almost the same as that of the control.

FIG. 10 shows the light and fluorescence microscopic images of dichlorofluorescin diacetate (DCFH-DA) analysis on untreated Wicell H1 cells and Wicell H1 cells treated with 12.5 µg/mL of JC011 after 3 hr. It can be seen that the ROS had decreased significantly in cells treated with JC011 compared to untreated cells. The untreated cells showed high ROS content as indicated by the bright green fluorescence (shown by arrows in FIG. 10A). The decrease in ROS content in the cells treated with JC011 indicates that JC011 is cytotoxic towards the hESCs (Wicell H1).

Figure 11A:
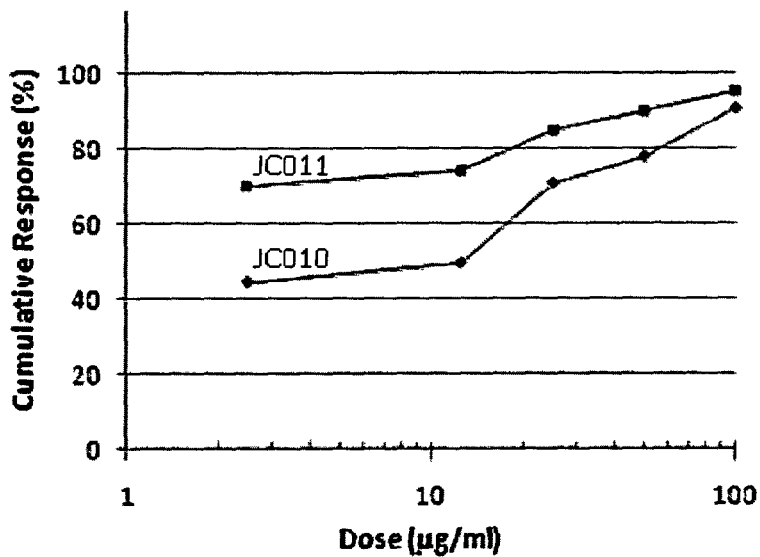
Figure 11B:
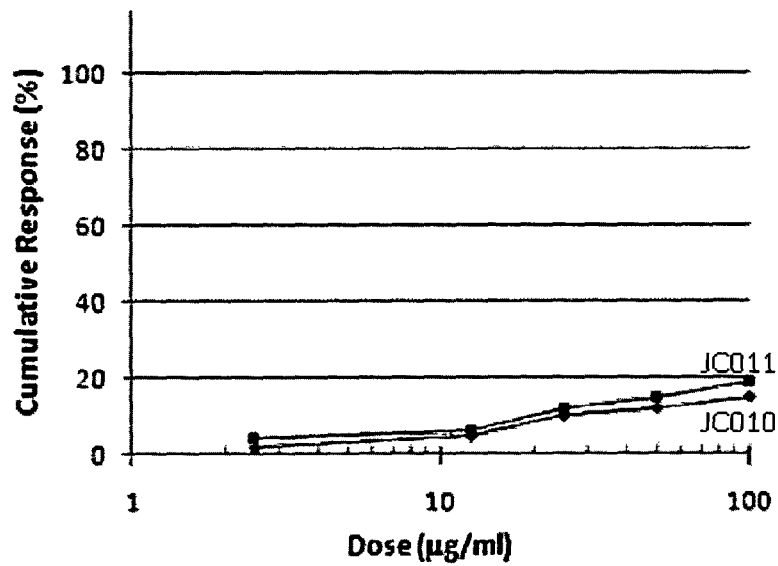

FIG. 11 shows the dose response curves for capsaicin analogues JC010 and JC011 on undifferentiated hESCs (FIG. 11A) and differentiated cells (FIG. 11B). From the dose response curve in FIG. 11A, the IC50 for JC010 was about 2.5 µg/mL while the IC50 for JC011 was at the nanogram level. In other words, JC010 and JC011 were very cytotoxic against undifferentiated hESCs. It can also be seen from the dose response curve in FIG. 11B, that both analogues were not cytotoxic to differentiated cells.

EXAMPLE 7

IPSC-selective Killing Induced by JC011

FIG. 12 shows the cytotoxic effect of the analogue JC011 (administered at a concentration of 12 µg/mL) on two IPSC cell lines, IPS-DF19-9 and IPS-foreskin, using the resazurin cell viability assay. Compared to the control, about 67% of the IPS-DF19-9 cells were killed by JC011 while about 62% of the IPS-foreskin cells were killed by JC011. Only 33% of the IPS-DF19-9 cells and 38% of the IPS-foreskin cells remained alive after a 16-hour exposure to the analogue JC011. Hence, in addition to hESCs, the analogue JC011 is also able to selectively kill IPSCs, which are known to be identical to ESCs in many aspects as discussed herein.

EXAMPLE 8

CSC-selective Killing Induced by Analogues JC010, JC011, JC017, JC040, JC048, JC049 and JC050

Seven analogues having different side chain lengths (JC010, JC011, JC017, JC040, JC048, JC049 and JC050) were tested for their cytotoxic effect on CSCs using the resazurin cell viability assay. Two CSC cell lines were used, a colon CSC cell line (Celprogen Cat#36112-39P-T25) and a breast CSC cell line (Celprogen Cat#36102-29P-T25).

The cytotoxic effect of the analogues JC010, JC011, JC017, JC040, JC048, JC049 and JC050 on the colon CSC cell line is shown in FIG. 13. Analogues JC040 and JC048 resulted in almost 45% cell death, while analogues JC010, JC011, JC017 and JC049 resulted in between about 15% to about 33% cell death. From these results, analogues with chain lengths of between 9 and 11 carbon atoms appear to have a higher cytotoxic effect on the colon CSCs.

With the breast CSCs, the data in FIG. 14 shows that analogue JC048 exhibited the highest cytotoxic effect causing almost 55% cell death, analogues JC040, JC049 and JC050 exhibited intermediate cytotoxic effect causing between 25% to 35% cell death, and analogues JC010, JC011 and JC017 exhibited relatively lower cytotoxic effect causing only about 15% cell death.

These data demonstrate that the analogues disclosed herein not only have cytotoxic effect on ESCs (such as hESCs) and IPSCs, but also on CSCs (such as colon and breast CSCs). In addition, the data also suggests that the length of the side chain in the analogues disclosed herein play a significant role in conferring the cytotoxic activity to these compounds. The analogue, having a side chain length of 11 carbon atoms, showed highest cytotoxic activity on both types of CSC cell lines, causing about 45% cell death in the colon CSC cell line and about 55% cell death in the breast CSC cell line.

EXAMPLE 9

Selective Killing of Dedifferentiated Stem Cells Induced by Analogues

Dedifferentiated stem cells are prepared using standard methods known in the art. The analogues prepared in Examples 1 to 3 are administered to the dedifferentiated stem cell preparations, and the cytotoxic effects of the analogues are assayed using the resazurin cell viability assay. It is expected that the analogues prepared in Examples 1 to 3 are able to exert a cytotoxic effect on the dedifferentiated cell preparations as seen with the hESC, CSC and IPSC cells in Examples 6, 7 and 8 above.

COMPARATIVE EXAMPLE

In summary, the above experimental data showed that the capsaicin analogues disclosed herein are cytotoxic against undifferentiated cells such as ESCs, IPSCs and CSCs.

Analogues JC010, JC011 and JC017 exhibited particularly high cytotoxic effect on undifferentiated hESCs. Analogues JC040, JC048 and JC049, on the other hand, exhibited high cytotoxic effect on CSCs.

JC011 also appeared to exhibit the highest specificity compared to JC010 and JC017, while JC017 exhibited the lowest specificity because some feeder cells were also killed when treated with JC017. The cytotoxic effect of JC010 and JC011 on differentiated cells were relatively low. Analogues JC025 and JC026, on the other hand, did not exhibit any selective cytotoxic activity towards undifferentiated or dedifferentiated stem cells.

The selective killing of cells treated with JC010 and JC011 also occurred within a relatively short period of time, that is less than 12 h. In some instances, the selective killing effects were seen within 3 h of administering the compounds to the cells. The highly potent cytotoxic effects of these compounds were also seen at very low concentrations of the analogue compounds, that is as low as 2.5 µg/mL and 12.5 µg/mL (8 and 40 µM, respectively), compared to 100 µM for in vitro cytotoxic effect of capsaicin.

Applications

The active compounds disclosed herein have demonstrated selective cytotoxic activity against undifferentiated stem cells and dedifferentiated stem cells. The disclosed active compounds have very low or no cytoxicity to differentiated cells. Advantageously, by providing the selective cytotoxic activity, the disclosed active compounds are useful as cytotoxic agents in pharmaceutical compositions to treat a patient in need of cell therapy. The disclosed active compounds are also useful as cytotoxic agents to remove undifferentiated and dedifferentiated stem cells from a cell preparation for use in cell therapy.

The disclosed active compounds have very low toxicity to humans, and hence are ideal for use in medicine, particularly for use in medicines for treating patients in need of or undergoing cell therapy.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A method for removing undifferentiated stem cells or dedifferentiated stem cells from a sample comprising said cells, the method comprising administering to said sample an effective amount of a compound of the formula (I):

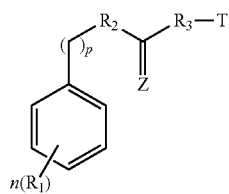

(I)

or a pharmaceutically acceptable salt thereof, wherein
n is an integer from 2 to 5;
p is an integer from 0 to 4;
$R_1$ is independently selected from the group consisting of a hydroxyl group, an alkoxy group, a thiol group, a thioether group and an amino group, wherein a first $R_1$ is on a carbon-3 position of the phenyl group and a second $R_1$ is on a carbon-4 position of the phenyl group, and the first $R_1$ and the second $R_1$ are selected from the group consisting of a hydroxyl group, a thiol group or an amino group;
$R_2$ and $R_3$ are independently a methylene group or a nitrogen nucleophile, with the proviso that at least one of $R_2$ and $R_3$ is a nitrogen nucleophile;
Z is an oxygen (O) atom or sulfur (S) atom; and
T is hydrogen or an optionally substituted aliphatic group.

2. A method of claim 1, wherein said cell sample further comprises differentiated cells.

3. A method of claim 2, further comprising the step of culturing the differentiated cells to prepare a cell population comprising differentiated cells.

4. The method of claim 1, wherein said undifferentiated stem cells or dedifferentiated stem cells are selected from the group consisting of human embryonic stem cells (hESC), induced pluripotent stem cells (IPSC) and cancer stem cells (CSC).

5. A method for preventing dedifferentiation of differentiated cells, the method comprising administering an effective amount of a compound of the formula(I):
or a pharmaceutically acceptable salt thereof, wherein
n is an integer from 2 to 5;
p is an integer from 0 to 4;
$R_1$ is independently selected from the group consisting of a hydroxyl group, an alkoxy group, a thiol group, a thioether group and an amino group, wherein a first $R_1$ is on a carbon-3 position of the phenyl group and a second $R_1$ is on a carbon-4 position of the phenyl group, and the first $R_1$ and the second $R_1$ are selected from the group consisting of a hydroxyl group, a thiol group or an amino group.

6. The method of claim 5, wherein said dedifferentiation occurs in vivo after transplantation of said differentiated cells in a patient in need of cell therapy.

7. A method of enriching for a population of differentiated cells from a cell population comprising differentiated cells, undifferentiated stem cells or dedifferentiated stem cells, the method comprising the step of contacting said cell population with an effective amount of a compound of the formula(I):

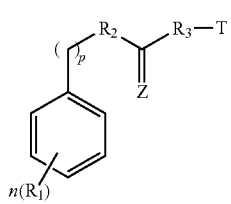

(I)

or a pharmaceutically acceptable salt thereof, wherein
n is an integer from 2 to 5;
is an integer from 0 to 4;
$R_1$ is independently selected from the group consisting of a hydroxyl group, an alkoxy group, a thiol group, a thioether group and an amino group, wherein a first $R_1$ is on a carbon-3 position of the phenyl group and a second $R_1$ is on a carbon-4 position of the phenyl group, and the first $R_1$ and the second $R_1$ are selected from the group consisting of a hydroxyl group, a thiol group or an amino group.

8. The method of claim 1, wherein the method is performed on a patient in need of cell therapy.

9. The method of claim 5, wherein the method is performed on a patient in need of cell therapy.

10. The method of claim 7, wherein the method is performed on a patient in need of cell therapy.

11. A method for removing undifferentiated stem cells or dedifferentiated stem cells from a sample comprising said cells, the method comprising administering to said sample an effective amount of a compound selected from the group consisting of:

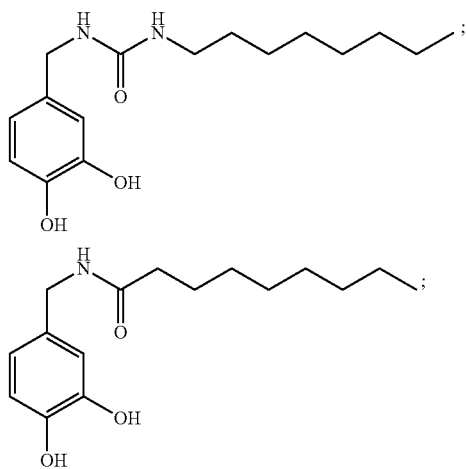

-continued
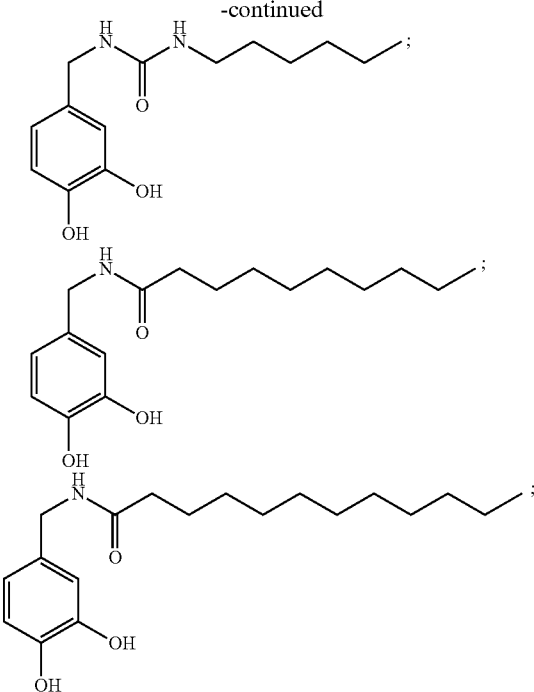
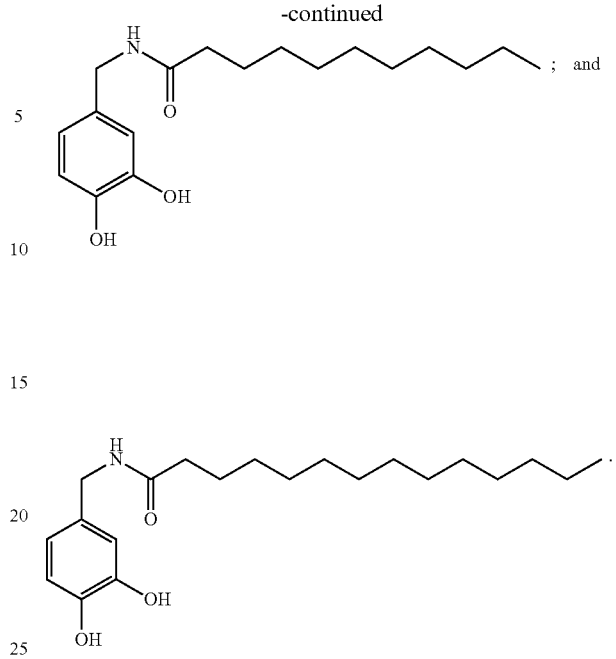
* * * * *